United States Patent
Sanchez et al.

(10) Patent No.: US 9,169,213 B2
(45) Date of Patent: Oct. 27, 2015

(54) METHOD OF WEIGHT MANAGEMENT

(71) Applicant: Arena Pharmaceuticals, Inc., San Diego, CA (US)

(72) Inventors: Matilde Sanchez, Alexandria, VA (US); William R. Shanahan, Del Mar, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 30 days.

(21) Appl. No.: 14/242,442

(22) Filed: Apr. 1, 2014

(65) Prior Publication Data

US 2014/0213579 A1    Jul. 31, 2014

Related U.S. Application Data

(63) Continuation of application No. 14/002,235, filed as application No. PCT/US2012/063711 on Nov. 6, 2012.

(60) Provisional application No. 61/711,413, filed on Oct. 9, 2012.

(51) Int. Cl.
   *C07D 223/16* (2006.01)
   *A61K 31/55* (2006.01)
   *A61K 31/137* (2006.01)

(52) U.S. Cl.
   CPC ............ *C07D 223/16* (2013.01); *A61K 31/137* (2013.01); *A61K 31/55* (2013.01)

(58) Field of Classification Search
   None
   See application file for complete search history.

(56) References Cited

U.S. PATENT DOCUMENTS

| | | |
|---|---|---|
| 2,900,415 A | 8/1959 | Biel |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |

(Continued)

FOREIGN PATENT DOCUMENTS

| | | |
|---|---|---|
| AU | 515 236 B2 | 3/1981 |
| CA | 1090797 | 12/1980 |

(Continued)

OTHER PUBLICATIONS

U.S. Appl. No. 60/372,058, filed Apr. 12, 2002, Smith et al.

(Continued)

Primary Examiner — San-Ming Hui
Assistant Examiner — Andrew Lee

(57) ABSTRACT

Provided are methods of determining if an individual is a responder to treatment with (R)-8-chloro-1-methyl-2,3,4,5-tetrahydro-1H-3-benzazepine or a pharmaceutically acceptable salt, solvate or hydrate thereof. Also provided are methods for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management. Also provided are methods for weight management in an individual in need thereof. Also provided are compounds, compositions, and kits for use in a method of weight management in an individual.

22 Claims, 2 Drawing Sheets

(56) References Cited

U.S. PATENT DOCUMENTS

| | | | |
|---|---|---|---|
| 4,233,217 A | 11/1980 | Shetty | |
| 4,477,378 A | 10/1984 | Gold et al. | |
| 4,541,954 A | 9/1985 | Borowski et al. | |
| 4,584,293 A | 4/1986 | Reiffen et al. | |
| 4,737,495 A | 4/1988 | Bomhard et al. | |
| 4,762,845 A | 8/1988 | Chu et al. | |
| 4,957,914 A | 9/1990 | Clark et al. | |
| 4,988,690 A | 1/1991 | Effland et al. | |
| 5,015,639 A | 5/1991 | Berger et al. | |
| 5,178,786 A | 1/1993 | Jahnke et al. | |
| 5,247,080 A | 9/1993 | Berger et al. | |
| 5,275,915 A | 1/1994 | Kojima et al. | |
| 5,387,685 A | 2/1995 | Powell et al. | |
| 5,397,793 A | 3/1995 | Shaber et al. | |
| 5,412,119 A | 5/1995 | Brussee et al. | |
| 5,422,355 A | 6/1995 | White et al. | |
| 5,691,362 A | 11/1997 | McCormick et al. | |
| 5,750,520 A | 5/1998 | Danilewicz et al. | |
| 5,795,895 A | 8/1998 | Anchors | |
| 5,856,503 A | 1/1999 | Aebi et al. | |
| 5,861,393 A | 1/1999 | Danilewicz et al. | |
| 5,908,830 A | 6/1999 | Smith et al. | |
| 5,925,651 A | 7/1999 | Hutchinson | |
| 5,939,415 A | 8/1999 | Laufer et al. | |
| 5,942,535 A | 8/1999 | Laufer et al. | |
| 5,958,943 A | 9/1999 | Laufer et al. | |
| 6,087,346 A | 7/2000 | Glennon et al. | |
| 6,218,385 B1 | 4/2001 | Adam et al. | |
| 6,900,313 B2 | 5/2005 | Wasserscheid et al. | |
| 6,953,787 B2 | 10/2005 | Smith et al. | |
| 6,972,295 B2 | 12/2005 | Hagmann et al. | |
| 7,105,523 B2 | 9/2006 | Stasch et al. | |
| 7,157,445 B2 | 1/2007 | Sanderink et al. | |
| 7,157,466 B2 | 1/2007 | McClure et al. | |
| 7,173,037 B2 | 2/2007 | Alonso-Alija et al. | |
| 7,211,591 B2 | 5/2007 | Tajima et al. | |
| 7,229,991 B2 | 6/2007 | Merla et al. | |
| 7,230,024 B2 | 6/2007 | Carpino et al. | |
| 7,232,823 B2 | 6/2007 | Carpino et al. | |
| 7,514,422 B2 | 4/2009 | Smith et al. | |
| 7,608,616 B1 | 10/2009 | Cartt | |
| 7,704,993 B2 | 4/2010 | Smith et al. | |
| 7,858,319 B2 | 12/2010 | Hetherington et al. | |
| 7,977,329 B2 | 7/2011 | Smith et al. | |
| 8,153,621 B2 | 4/2012 | Behan et al. | |
| 8,168,624 B2 | 5/2012 | Agarwal et al. | |
| 8,168,782 B2 | 5/2012 | Weigl et al. | |
| 8,207,158 B2 | 6/2012 | Smith et al. | |
| 8,273,734 B1 | 9/2012 | Smith et al. | |
| 8,299,241 B2 | 10/2012 | Gharbaoui et al. | |
| 2003/0105106 A1 | 6/2003 | Chiang et al. | |
| 2003/0225057 A1 | 12/2003 | Smith et al. | |
| 2004/0101575 A1 | 5/2004 | Hinz | |
| 2005/0020573 A1 | 1/2005 | Smith et al. | |
| 2007/0060568 A1 | 3/2007 | Smith et al. | |
| 2007/0275949 A1 | 11/2007 | Smith et al. | |
| 2008/0009478 A1 | 1/2008 | Smith et al. | |
| 2008/0045502 A1 | 2/2008 | Wolgast et al. | |
| 2008/0255093 A1* | 10/2008 | Tam et al. | 514/217.01 |
| 2009/0143576 A1 | 6/2009 | Weigl et al. | |
| 2010/0004223 A1 | 1/2010 | Agarwal et al. | |
| 2010/0173894 A1 | 7/2010 | Smith et al. | |
| 2010/0305316 A1 | 12/2010 | Gharbaoui et al. | |
| 2011/0015438 A1 | 1/2011 | Carlos et al. | |
| 2011/0065660 A1* | 3/2011 | Baron et al. | 514/26 |
| 2012/0135982 A1 | 5/2012 | Smith et al. | |
| 2012/0142967 A1 | 6/2012 | De Mattei et al. | |
| 2012/0252786 A1 | 10/2012 | Behan et al. | |
| 2012/0252787 A1 | 10/2012 | Anderson et al. | |
| 2012/0252788 A1 | 10/2012 | Smith et al. | |
| 2012/0264743 A1 | 10/2012 | Agarwal et al. | |

FOREIGN PATENT DOCUMENTS

| | | |
|---|---|---|
| CA | 2197789 | 2/1996 |
| CA | 2325741 | 10/1999 |
| CH | 500194 | 1/1971 |
| CN | 102126988 | 7/2011 |
| DE | 1944121 | 3/1970 |
| DE | 1914456 | 6/1971 |
| DE | 3315106 A1 | 11/1983 |
| DE | 3418270 A1 | 11/1985 |
| EP | 0 002 765 A1 | 7/1979 |
| EP | 0 027 695 B1 | 10/1980 |
| EP | 0 007 070 A1 | 1/1983 |
| EP | 0 807 79 B1 | 6/1983 |
| EP | 0 968 38 B1 | 12/1983 |
| EP | 0 161 350 A1 | 11/1985 |
| EP | 0 174 118 A3 | 3/1986 |
| EP | 0 080 779 B1 | 7/1986 |
| EP | 0 204 349 A2 | 12/1986 |
| EP | 0 096 838 A1 | 4/1987 |
| EP | 0 245 997 A2 | 11/1987 |
| EP | 0 285 287 A2 | 10/1988 |
| EP | 0 285 287 A3 | 10/1988 |
| EP | 0 331 130 A1 | 9/1989 |
| EP | 0 331 130 B1 | 9/1993 |
| EP | 0 285 919 B1 | 10/1994 |
| EP | 0 987 235 A1 | 3/2000 |
| EP | 1 074 549 A2 | 2/2001 |
| EP | 0 987 235 B1 | 3/2003 |
| EP | 1 074 549 B1 | 11/2003 |
| EP | 1 411 881 A2 | 4/2004 |
| EP | 1 411 881 B1 | 5/2005 |
| EP | 1 838 677 B1 | 9/2009 |
| FR | 2 518 544 A1 | 6/1983 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 1599705 | 10/1981 |
| GB | 2133401 | 7/1984 |
| JP | 62-267250 | 11/1987 |
| JP | 2-502723 | 8/1990 |
| JP | 5-339263 | 12/1993 |
| JP | 6-62574 | 8/1994 |
| JP | 6-298746 | 10/1994 |
| JP | 8-134048 | 5/1996 |
| JP | 9-30960 | 2/1997 |
| JP | 9-87258 | 3/1997 |
| JP | 2000-44533 | 2/2000 |
| JP | 2001-76413 | 3/2001 |
| JP | 2001-89472 | 4/2001 |
| NL | 7807819 | 7/1978 |
| SU | 1238732 A3 | 6/1986 |
| WO | WO 88/07526 A1 | 10/1988 |
| WO | WO 88/07858 A1 | 10/1988 |
| WO | WO 91/19698 A1 | 12/1991 |
| WO | WO 93/00094 A2 | 1/1993 |
| WO | WO 93/03015 A1 | 2/1993 |
| WO | WO 93/16997 A1 | 9/1993 |
| WO | WO 95/13274 A1 | 5/1995 |
| WO | WO 96/04271 A1 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 A1 | 9/2002 |
| WO | WO 03/000663 A1 | 1/2003 |
| WO | WO 03/027068 A2 | 4/2003 |
| WO | WO 03/057161 A2 | 7/2003 |
| WO | WO 03/062205 A1 | 7/2003 |
| WO | WO 03/062392 A2 | 7/2003 |
| WO | WO 03/086306 A2 | 10/2003 |
| WO | WO 03/086306 A3 | 2/2004 |

(56) References Cited

FOREIGN PATENT DOCUMENTS

| | | |
|---|---|---|
| WO | WO 2004/037788 A1 | 5/2004 |
| WO | WO 2005/003096 A1 | 1/2005 |
| WO | WO 2005/016902 A1 | 2/2005 |
| WO | WO 2005/019179 A2 | 3/2005 |
| WO | WO 2005/019179 A3 | 3/2005 |
| WO | WO 2005/019180 A1 | 3/2005 |
| WO | WO 2005/042490 A1 | 5/2005 |
| WO | WO 2005/042491 A1 | 5/2005 |
| WO | WO 2005/082859 A1 | 9/2005 |
| WO | WO 2006/006933 A2 | 1/2006 |
| WO | WO 2006/013209 A2 | 2/2006 |
| WO | WO 2006/043710 A1 | 4/2006 |
| WO | WO 2006/069363 A2 | 6/2006 |
| WO | WO 2006/071740 A2 | 7/2006 |
| WO | WO 2006/069363 A3 | 5/2007 |
| WO | WO 2007/120517 A2 | 10/2007 |
| WO | WO 2007/120517 A3 | 6/2008 |
| WO | WO 2008/070111 A2 | 6/2008 |
| WO | WO 2008/070111 A3 | 8/2008 |
| WO | WO 2008/153632 A2 | 12/2008 |
| WO | WO 2008/156707 A1 | 12/2008 |
| WO | WO 2009/080691 A2 | 7/2009 |
| WO | WO 2009/097416 A1 | 8/2009 |
| WO | WO 2009/111004 A1 | 9/2009 |
| WO | WO 2010/148207 A2 | 12/2010 |
| WO | WO 2012/030927 A2 | 3/2012 |
| WO | WO 2012/030938 A1 | 3/2012 |
| WO | WO 2012/030951 A1 | 3/2012 |
| WO | WO 2012/030953 A1 | 3/2012 |

OTHER PUBLICATIONS

U.S. Appl. No. 60/405,495, filed Aug. 23, 2002, Smith et al.
U.S. Appl. No. 60/434,607, filed Dec. 18, 2002, Smith et al.
U.S. Appl. No. 60/479,280, filed Jun. 17, 2003, Smith et al.
U.S. Appl. No. 60/512,967, filed Oct. 21, 2003, Burbaum et al.
U.S. Appl. No. 60/638,221, filed Dec. 21, 2004, Agarwal et al.
U.S. Appl. No. 60/789,191, filed Apr. 3, 2006, Lu et al.
U.S. Appl. No. 60/873,036, Dec. 5, 2006, Gharbaoui et al.
U.S. Appl. No. 61/068,102, filed Mar. 4, 2008, Carlos et al.
U.S. Appl. No. 61/268,930, filed Jun. 18, 2009, Demattei et al.
"Arena Pharmaceuticals Announces Assessment of Echocardiograms Indicates No Apparent APD356 Effect on Heart Valves or Pulmonary Artery Pressure in Phase 2a Trial," Press Release, Arena Pharmaceuticals, Inc., 3 pages (Aug. 25, 2005).
"Arena Pharmaceuticals Announces Initiation of Phase 2b Clinical Trial of its Novel Anti-Obesity Compound," Press Release, Arena *Pharmaceuticals*, Inc., 3 pages (Jun. 23, 2005).
"Arena Pharmaceuticals Announces Lorcaserin Phase 2b Clinical Trial Results Published in *Obesity*," Press Release, Arena Pharmaceuticals, Inc., 3 pages (Dec. 8, 2008).
"Arena Pharmaceuticals Announces Positive Phase 2 Clinical Trial Results of Novel Anti-Obesity Compound," Press Release, Arena Pharmaceuticals, Inc., 4 pages (May 11, 2005).
"Arena Pharmaceuticals Announces Positive Phase 2b Clinical Trial Results of Novel Anti-Obesity Compound," Press Release, Arena Pharmaceuticals, Inc., 5 pages (Dec. 13, 2005).
"Arena Pharmaceuticals Announces Results of its Phase 1b Safety Study for its Novel Anti-Obesity Compound," Press Release, Nov. 30, 2004, 2 pages.
"Arena Pharmaceuticals Completes Enrollment with 3,182 Patients in Lorcaserin Phase 3 BLOOM Trial for Obesity," Press Release, Arena Pharmaceuticals, Inc., 3 pages (Feb. 5, 2007).
"Arena Pharmaceuticals Continues Phase 3 BLOOM Obesity Trial Following Independent Echocardiographic Data Safety Monitoring Board Review," Press Release, Arena Pharmaceuticals, Inc., 3 pages (Sep. 11, 2007).
"Arena Pharmaceuticals Enters into Strategic Agreements for the Manufacture of Pharmaceutical Material, Including Lorcaserin," Press Release, Arena Pharmaceuticals, Inc., 3 pages (Dec. 18, 2007).
"Arena Pharmaceuticals Initiates Clinical Trial of Novel Anti-Obesity Drug," Press Release, Feb. 24, 2004, 1 page.
"Arena Pharmaceuticals Initiates Lorcaserin Phase 3 Obesity Clinical Trial," Press Release, Arena Pharmaceuticals, Inc., 3 pages (Sep. 12, 2006).
"Arena Pharmaceuticals Initiates Phase 1b Clinical Trial of Novel Anti-Obesity Drug," Press Release, Jul. 26, 2004, 1 page.
"Arena Pharmaceuticals Initiates Phase 2 Efficacy Study for its Novel Anti-Obesity Compound," Press Release, Dec. 22, 2004, 2 pages.
"Arena Pharmaceuticals Initiates Second and Third Pivotal Trials Evaluating Lorcaserin for the Treatment of Obesity," Press Release, Arena Pharmaceuticals, Inc., 4 pages (Dec. 13, 2007).
"Arena Pharmaceuticals Provides APD356 Obesity and APD125 Insomnia Clinical Program Updates," Press Release, Arena Pharmaceuticals, Inc., 3 pages (Mar. 29, 2006).
"Arena Pharmaceuticals Reports Successful Phase 1a Safety and Clinical Pharmacology Trial Results of Novel Anti-Obesity Compound," Press Release, Jul. 14, 2004, 2 pages.
"Arena Pharmaceuticals' APD356 Selected as Winner of CONNECT's Most Innovative New Product Award in the Biotechnology Research and Development Category," Press Release, Arena Pharmaceuticals, Inc., 3 pages (Dec. 12, 2005).
"Arena Pharmaceuticals' Lorcaserin for Obesity Passes Major Safety Milestone," Press Release, Arena Pharmaceuticals, Inc., 4 pages (Mar. 17, 2008).
"Arena Pharmaceuticals' Lorcaserin Hydrochloride Phase 2b Study Results Demonstrate Significant Weight Loss and Positive Effect on BMI and Waist and Hip Circumference in Obese Patients," Press Release, Arena Pharmaceuticals, Inc., 4 pages (Jun. 12, 2006).
"Arena's APD356 Phase 2a Clinical Trial Data Presented at the 2005 NASSO Annual Meeting," Press Release, Arena Pharmaceuticals, Inc., 3 pages (Oct. 18, 2005).
"FDA approves Belviq to treat some overweight or obese adults", Home Healthcare Nurse vol. 30, No. 8, Jan. 1, 2012, pp. 443-444.
"Guidance for Industry, Pharmacokinetics in Patients with Impaired Renal Function—Study Design, Data Analysis, and Impact on Dosing and Labeling", FDA (1998).
"Intracellular 5-HT2c-receptor dephosphorylation: a new target for treating drug addiction," Trends in Pharmacological Sciences, 27(9):455-58(2006).
"Silver Lining to the Cloud Over Anorexogen-Related Cardiac Valvulpathy?" Editorial, Annals of Internal Medicine, 134(4): 335-337 (2001).
Anderson et al., "Dose Selection and Design of Phase 3 Clinical Trials: Efficacy and Safety of Lorcaserin for Weight Management," presented at the Obesity Society (2008).
Anderson et al: "Lorcaserin, a Selective 5-HT2c Agonist, Is Efficacious for Weight Loss across Patient Subgroups", Diabetes, vol. 59, No. Suppl. 1, Jun. 1, 2010, p. A482.
Anderson, "Pharmacokinetic Properties of Lorcaserin in Subjects With Renal Impairment", Jul. 27, 2009.
Arena Pharmaceuticals Research & Development Day, Powerpoint presentations from Meeting, 141 pages, Dec. 15, 2008.
Arena Pharmaceuticals Research & Development Day, Powerpoint presentations from Meeting, 182 pages, Nov. 9, 2006.
Arena Pharmaceuticals Research & Development Day, Transcript of Meeting, 36 pages, Dec. 15, 2008.
Arena Pharmaceuticals Research & Development Day, Transcript of Meeting, 36 pages, Nov. 9, 2006.
Bagnol et al., "Obesity and Hypothalamic Signaling: Role of GPCRs," Presentation, Arena Pharmaceuticals, Inc., Jul. 30, 2010, 30 pages.
Baindur et al., "(±)-3-Allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship," J. Med. Chem., 35:67-72 (1992).
Barbière, "Estérification Nitrique et Nitration d'Amino-alcools," Bulletin de la SociétéChimique de France, 5(11):470-480 (1944).
Barnes, "Pharmacological Strategies for Relapse Prevention in Schizophrenia," Psychiatry 3(10): 37-40 (2004).
Barnes, Pharmacological Strategies for Relapse Prevention in Schizophrenia, Psychiatry, 3(10):37-40 (2004).
Belviq Prescribing Information Jun. 2012.

(56) References Cited

OTHER PUBLICATIONS

Berge et al., "Pharmaceutical Salts," Journal of Pharmaceutical Sciences 66(1):1-19 (1977).
Bickerdike, "5-HT2C Receptor Agonists as Potential Drugs for the Treatment of Obesity," Current Topics in Medicinal Chemistry, 3:885-897 (2003).
Biel, "Bronchodilators, N-substituted Derivatives of 1-(3',4'-Dihydroxyphenyl)-2-aminoethanol (Arterenol)," J. Am. Chem. Soc. 76:3149-3153 (1954).
Binetti et al. "Behavior Disorders in Alzheimer Disease: A Transcultural Perspective.," Arch Neurol., 55:539-544 (1998).
Bjenning et al., "Chronic Oral Administration of APD356 Significantly Reduces Body Weight and Fat Mass in Obesity-Prone (DIO) Male and Female Rats," presented at the European Conference on Obesity, Prague (2004).
Bjenning et al., "Increased Sensitivity in Female Obesity-Prone Rats to the Weight-loss Effect o APD 356 A Selective 5-HT2c Agonist," presented at the Annual North American Association for the Study of Obesity, Las Vegas, NV, (2004).
Bos et al., "Novel Agonists of 5HT2C receptors. Synthesis & biological evaluation of Substituted 2-{Indol-1-yl)-1-methylethylamines and 2-(Indeno[1,2-b]pyrrol-1-yl)-1-methylethylamines," Improved Therapeutics for Obsessive Compulsive Disorder, J. Med. Chem. 40(17):2762-2769 (1997).
Bosch et al., "Studies on the Synthesis of Pentacyclic Strychnos Indole Alkaloids. Photocyclization of N-Chloroacetyl-l,2,3,4,5,6-hexahydro-1,5-methanoazocino [4,3-b] Indole Derivatives," Tetrahedron, 41(12):2557-66 (1985).
Bremner "Seven Membered Rings," Institute for Biomolecular Science, Dept. of Chemistry, University of Wollongong; "Progress in Heterocyclic Chemistry 13," Pergamon Press, Ch. 7:340-77 (2001).
Byrn et al., "Pharmaceutical solids: A strategic approach to regulatory consideration," Pharmaceutical Research 12(7):945-954 (1995).
Caira, "Crystalline polymorphism of organic compounds," Topics in Current Chemistry 198(2): 163-208 (1998).
Callahan et al., "Fluoxetine Increases the Anorectic and Long-Term Dopamine-Depleting Effects of Phentermine," Synapse, 38(4):471-6 (2000).
Carey, F and Sunderg, R., "Advanced Organic Chemistry, Part B: Reactions and Synthesis, second edition" 1983, Plenum Press, New York, pp. 96-98.
CAS Registry No. 006640-24-01 (2007).
CAS Registry No. 149454-12-6 (1993).
CAS Registry No. 27487-50-9 (1984).
CAS Registry No. 27487-51-0 (1984).
CAS Registry No. 400878-20-8 (2002).
CAS Registry No. 46906-45-0 (1984).
CAS Registry No. 620948-34-7 and 620948-93-8 (2007).
Casy, et al., "Some Arylalkylamino Analogs of Acyclic Analgetics," J. Med. Chem., 11(3):599-601 (1968).
Cerny et al., "Kinetics of N-Carbamoyl Glucuronide Formation," presented at N. American ISSX (2008).
Cerny, et al., "Formation of N-Carbamoyl Glucuronide Metabolite of Lorcaserin." Drug Metab Rev 2008, 40(Suppl. 3): Abst 92.
Chahal et al., IDdb Meeting Report 2000, May 17-18.
Chang et al., "Dopamine Receptor Binding Properties of Some 2,3,4,5-tetrahydro-1H-3-benzazepine-7-ols with Non-Aromatic Substituents in the 5-Position," Bioorganic & Medicinal Chemistry Letters, 2(5):399-402 (1992).
Chemical abstract (online) Accession No. 1980:407990.
Chen et al., "Metabolism and Disposition of Lorcaserin, A Novel Selective Serotonin 5-HT2C Receptor Agonist, in Rats, Mice, Monkeys and Humans," presented at the European ISSX (2008).
Chen et al., "Metabolism, Pharmacokinetics, & Excretion of Lorcaserin, A Novel Selective Serotonin 5-HT2C Receptor Agonist, in Healthy Male Volunteers," presented at N. American ISSX (2008).
Chen, et al., "Metabolism and Disposition of Lorcaserin, A Novel Selective Serotonin 5-HT2C Receptor Agonist, in Rats, Mice, Monkeys and Humans." Drug Metab Rev 2008, 40(Suppl. 1): Abst 185.
Chen, et al., "Metabolism, Pharmacokinetics, and Excretion of Lorcaserin, A Novel Selective Serotonin 5-HT2C Receptor Agonist, in Healthy Male Volunteers." Drug Metab Rev 2008, 40(Suppl. 3): Abst 281.
Cheng, "Fen/Phen and Valvular Heart Disease: The Final Link Has Now Been Established," Circulation 2000;102;e180.
Chumpradit et al., "($\pm$)-7-Chloro-8-hydroxy-1-(4'[125I]iodophenyl)-3-methyl-2,3,4,5-tetrahydro-1H-3-benzazepine: A Potential CNS D-1 Dopamine Receptor Imaging Agent," J. Med. Chem., 32:1431-35 (1989).
Clark et al., "1,9-Alkano-bridged 2,3,4,5-tetrahydro-1 H-3-benzazepines with Affinity for the $\alpha$2-Adrenoceptor and the 5-HT1A Receptor," J. Med. Chem., 33:633-41 (1990).
Clinical Trial NCT00768612. "Study Evaluating Safety and Tolerability of Vabicaserin in Patients With Sudden Worsening of Schizophrenia Study," (2008).
Connolly et al., "Selections from Current Literature: Pharmacological Treatment of Obesity," Family Practice, 15(1):88-93 (1998).
Deady et al., "Synthesis of Some Tetrahydro-2- and 3-benzazepines, and of Hexahydro-3-benzazocine," JCS Perkin I, 782-3 (1973).
Demarinis et al., "Development of an Affinity Ligand for Purification of $\alpha$2-Adrenoceptors from Human Platelet Membranes," J. Med. Chem., 27:918-921 (1984).
Dhonnchadha et al., "Anxiolytic-Like Effects of 5-HT2 Ligands on Three Mouse Models of Anxiety," Behav. Brain Res. 140:203-214 (2003).
Di Chiara et al., "Nucleus Accumbens Shell and Core Dopamine: Differential Role in Behavior and Addiction," Behavioural Brain Research, 137: 75-114 (2002).
Di Chiara et al., "Reward System and Addiction: What Dopamine Does and Doesn't Do," Current Opinion in Pharmacology 7:69-76 (2007).
Di Giovanni et al., "Serotonin/Dopamine Interaction—Focus on 5-HT2C Receptor, A New Target of Psychotropic Drugs," Indian Journal of Experimental Biology, 40:1344-1352 (2002).
Di Matteo et al., "Role of 5-HT2C Receptors in the Control of Central Dopamine Function," Trends in Pharmacological Sciences, 22(5):229-232 (2001).
Diagnostic and Statistical Manual of Mental Disorders, 4th edition, Text Revision, Washington, DC, American Psychiatric Association, 2000.
Dixit et al. "Agents Acting on Central Nervous System: Part XXIII-2-Substituted 1, 2, 3, 4, 6, 7, 12, 12a-Octahydropyrazino[2,1-b][3] benzazepines & 3-Substituted 1, 2, 3, 4, 4a, 5, 6, 11-Octahydropyrazino[I,2-b][2] benzazepines," CDRI Communication No. 1969, 893-97 (1974).
Draper et al., "Novel Stereoselective Syntheses of the Fused Benzazepine Dopamine D1 Antagonist (6aS, 13bR)-11-chloro-6,6a,7,8,9, 13b-hexahydro-7-methyl-5H-benzo[d]naphth[2,1-b]azepin-12-ol (Sch 39166): 1. Aziridinium Salt Based Syntheses," Organic Process Research & Development, 2(3):175-85 (1998).
Endocrinologic and Metabolic Drugs Advisory Committee Meeting United States Food & Drug Administration Center for Drug Evaluation and Research (May 10, 2012).
FDA Briefing Document: Lorcaserin Hydrochloride Tablets, 10 mg, United States Food & Drug Administration Endocrinologic and Metabolic Drugs Advisory Committee Meeting (May 8, 2012).
Fidler et al: "A One-Year Randomized Trial of Lorcaserin for Weight Loss in Obese and Overweight Adults: The BLOSSOM Trial", Journal of Clinical Endocrinology & Metabolism, vol. 96, No. 10, Oct. 1, 2011, pp. 3067-3077.
Fidler et al: "Changes in Glucose Tolerance and Cardiovascular Risk Factors after 52 Weeks of Treatment with Lorcaserin", Diabetes, vol. 59, No. Suppl. 1, Jun. 1, 2010, pp. A484-A485.
Flannery-Schroeder, "Reducing Anxiety to Prevent Depression," Am. J. Prev. Med. 31 (6S1):S136-S142 (2006).
Frankel et al., "Brain Serotonin Transporterdistribution in Subjects With Impulsive Aggressivity: A Positron Emission Study With [11C]McN 5652." Am. J. Psychiatry,162:915-923 (2005).
Fuchs et al., "Total Synthesis of (+/-)-Lennoxamine and (+/-)-Aphanorphine by Intramolecular Electrophilic Aromatic Substitution Reactions of 2-Amidoacroleins," Organic Letters, 3(24):3923-3925 (2001).

(56) References Cited

OTHER PUBLICATIONS

Gallant et al., "U-22,394A: A Controlled Evaluation in Chronic Schizophrenic Patients," Current Therapy Research, 9(11):579-81(1967).
Gardent et al., "Sur Quelques Proprietes De L'amino-2-Bromo-4 1H Benzazepine-3 Et De Ses Derives," Bulletin de la Societe Chimique de France, 2:600-5 (1968).
Garrido., Form and Structure of Crystals, Chapter V, p. 204.
Garrison, "Defining Obesity: An Adventure in Cardiovascular Disease Epidemiology," J. Nutritional Biochem. 9(9):493-500 (1998).
Gerace et al., "Predictors of Weight Increases over 7 Years in Fire Fighters and Paramedics," Preventive Medicine 25:593-600 (1996).
Gerritz et al., "Two General Routes to 1,4-Disubstituted-2,3,4,5-tetrahydro-1H-3-benzazepines," Organic Letters, 2(25):4099-102 (2000).
Gobert et al., "Serotonin2c Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).
Goldenberg: "Pharmaceutical approval update", P & T Pharmacy and Therapeutics Journal, vol. 37, No. 9, Sep. 1, 2012, pp. 499-502.
Gombar et al., "Pharmacokinetics of a Series of 6-Chloro-2, 3, 4, 5-Tetrahydro-3-Substituted-1 H-3-Benzazepines in Rats," Drug Metab. Disposition ,16:367-372 (1988).
Greene et al., Protective Groups in Organic Syntheses, 2nd Ed., Wiley and Sons, NY (1991)* *ref excessively voluminous; provided upon request.
Greene, "Protective Groups in Organic Synthesis," 3rd Ed., Wiley and Sons (1999)* ref excessively voluminous; provided upon request.
Griesser "Polymorphism in the Pharmaceutical Industry," ed. Rolf Hilfier, Wiley-VCH Verlag GmbH & Co.: pp. 211-233 (2006).
Grottick Etal.,"Lorcaserin: A Selective 5-HT2c Agonist for Weight Management," presented at the Annual North American Association for the Study of Obesity,(2007).
Guillory, "Polymorphism in Pharmaceutical Solids," ed. Harry G. Brittain, Marcel Dekker, Inc., vol. 95: pp. 202-209 (1999).
Halford et al., "Serotonergic Drugs: Effects on Appetite Expression and Use for the Treatment of Obesity," Drugs 67(1):27-55 (2007).
Halford et al., "o-Phenylenediacetimide and Other Compounds Related to 3,1 H-benzazepine," J. Org. Chem., 17:1646-52 (1952).
Halford, "Obesity Drugs in Clinical Development," Current Opinion in Investigational Drugs 7(4):312-318 (2006).
Hasan et al., "Syntheses of N-Chloroacyl-β-phenylethylamine Derivatives," Indian J. Chem., 9:1022-4 (1971).
Hashima et al., "Syntheses and Biological Activities of the Marine Bryozoan Alkaloids Convolutamines A, C and F and Lutamides A and C," Bioorg & Med. Chem., 8:1757 (2000).
Hassine-Coniac, et al., "Preparation Et Propriétés D'aldéhydes Dans La Série De La Benzazépine-3," Bulletin de La SociétéChimique de France, 11:3985-92 (1971) French Lang Only.
Haynes et al., "Occurrence of Pharmaceutically Acceptable Anions and Cations in the Cambridge Structural Database," J. Pharm. Sci. 94(10):2111-2120 (2005).
Hazebroucq, "Accés A Des I-H, Tétrahydro-2, 3, 4,5 Benzazépines-3 One-I, et a Des Hexahydro Imidazo Isoquinoléines," Ann. Chim., t.1:221-54 (1966) French Lang Only.
Heisler et al., "Activation of Central Melanocortin Pathways by Fenfluramine," Science, 297:609-611 (2002).
Helferich et al., "Uber Derivate Einger Chinolincarbonsauren," J. Fur Praktische Chemie, 33:39-48(1966).
Hester et al., "Azepinoindoles. I. Hexahydroazepino[4,5-b]indoles," J. Med. Chem., 11(1): 101-106 (1968).
Heys et al., "A New Entry into C7-Oxygenated Tetrahydro-1 H-3-benzazepines: Efficient Labeling with Carbon-14 in the Benzo Ring," J. Org. Chem., 54(19):4702-6 (1989).
Higgins et al. "Serotonin and Drug Reward: Focus on 5-HT2C Receptors," European Journal of Pharmacology, 480: 151-162 (2003).

Hitzig, "Combined Serotonin and Dopamine Indirect Agonists Correct Alcohol Craving and Alcohol-Associated Neuroses," Journal of Substance Abuse Treatment, 11(5):489-90 (1994).
Ichii, "Friedel-Crafts Aralkylation. II. The AICl3 CH2NO2-Catalyzed Phenethylation of Benzene and Toluene With 2-Arylethyl Chlorides in a Nitromethane Solution," Bulletin of the Chemical Society of Japan, 45(9):2810-2813 (1972).
Im et al., "Positive Allosteric Modulator of the Human 5-HT2C Receptor," Molecular Pharmacology, 64: 78-84 (2003).
Isaac, "The 5-HT2C Receptor As a Potential Therapeutic Target for the Design of Antiobesity and Antiepileptic Drugs," Drugs of the Future 26(4), 383-393 (2001).
Jandacek, "APD-356 (Arena)," Current Opinion in Investigational Drugs 6(10):1051-1056 (2005).
Jenck, et al., "Antiaversive Effects of 5HT2C Receptor Agonists and Fluoxetine in a Model of Panic-Like Anxiety in Rats," European Neuropsychopharmacology 8: 161 (1998).
Jensen et al., "Potential Role of New Therapies in Modifying Cardiovascular Risk in Overweight Patients with Metabolic Risk Facts," Obesity 14 (Suppl. 3):143S-149S (2006).
Kaiser et al., "6-(Phenylthio)-substituted 2,3,4,5-tetrahydro-1H-3-benzazepines, A Novel Class of Dopamine Receptor Antagonists and Neuroleptics," J. Med. Chem., 23(9):975-6 (1980).
Karasu et al., Practice Guideline for the Treatment of Patients with Major Depressive Disorder (2000).
Klein, "Outcome Success in Obesity," Obesity Res., 9(suppl. 4):3545-358S (2001).
Klohr et al., "An Intramolecular Photocyclization to Form the Azepino[3,4,5-cd]Indole System," Synthetic Communications 18(7):671-4 (1988).
Koplan et al., "Preventing Childhood Obesity: Health in the Balance, Executive Summary," The National Academies Press, Washington, D.C., 436 pages (excerpt includes pp. 1-19, v-xix) (2005).
Krull et al., "Synthesis and Structure/NMDA Receptor Affinity Relationships of 1-Substituted Tetrahydro-3-Benzazepines,"Bioorganic & Medicinal Chem. 12(6):1439-1451 (2004).
Kuenburg et al., "Development of a Pilot Scale Process for the Anti-Alzheimer Drug (—)-Galanthamine Using Large-Scale Phenolic Oxidative Coupling and Crystallisation-Induced Chiral Conversion," Organic Process Research & Development, 3(6):425-31 (1999).
Lacivita et al., "Selective Agents for Serotonin2C (5-HTC2C) Receptor," Current Topics in Medicinal Chemistry, 6: 1927-1970 (2006).
Ladd et al., "Synthesis of a Dopaminergic Binding of 2-Aryldopamine Analogues: Phenethylamines, 3-Benzazepines, and 9-(Aminomethyl) Fluorenes," J. Med. Chem., 29(10):1904-12 (1986).
Lam et al., Canadian Consensus Guidelines for the Treatment of Seasonal Affective Disorder, Clinical & Academic Publishing, Vancouver, BC, Canada (1999).
Lanteri et al., "Drugs of abuse specifically sensitive noradrenergic and serotonergic neurons via a non-dopaminergic mechanism," Neuropsychopharmacology 33(7):1724-1734 (2008).
Lennon et al., "Azabenzocycloheptenones. Part XVIII. Amines and Amino-ketones of the Tetrahydro-3-benzazepin-1-one Series," J.C. S. Perkin 1, 7:622-6 (1975).
Lin et al, "Benzindene Prostaglandins. Synthesis of Optically Pure 15-Deoxy-U-68,215 and its Enantiomer via a Modified Intramolecular Wadsworth-Emmons-Wittig Reaction," J. Org. Chem., 52(25):5594-601 (1987).
Loke et al., "Appetite Suppressants and Valvular Heart Disease—A Systematic Review," BMC Clinical Pharmacology, 2(6):1-10 (2002).
Lorcaserin for Weight Management, United States Food & Drug Administration Center for Drug Evaluation & Research (May 10, 2012).
MacDonald et al., "Design and Synthesis of trans-3-(2-(4-((3-(3-(5-methyl-1,2,4-oxadiazolyl))-phenyl)carboxamido)cyclohexyl)ethyl)-7-methylsulfonyl-2,3,4,5-tetrahydro-1H-3-benzazepine (SB-414796): A Potent and Selective Dopamine D3 Receptor Antagonist," J. Med. Chem., 46(23):4952-64 (2003).
March, "Advanced Organic Chemistry, Reactions, Mechanisms and Structure; Third edition," 1985, John Wiley &Sons (Wiley-Interscience Publication), New-York, pp. 382-384.

(56) References Cited

OTHER PUBLICATIONS

Martin et al.,"5HT2C Receptor Agonists Pharmacological Characteristics and Therapeutic Potential," J. Pharmacol. Exp. Therap., 286(2):913-924 (1998).

Menzaghi et al., "APD356, a Selective 5-HT2c Receptor Agonist As a Potential Novel Treatment for Obesity," presented at the 33rd Annual Society of Neuroscience Meeting New Orleans, LA, (2003).

Millan et al., "Serotonin (5-HT)2C receptors tonically inhibit dopamine (DA) and noradrenaline (NA), but not 5-HT, release in the frontal cortex in vivo," Neuropharmalogy 37(7):953-955 (1998).

Millan et al., "5HT2C Receptors Mediate Penile Erections in Rats: Actions of Novel and Selective Agonists and Antagonists." Eur. J. Pharmacol., 325:9-12 (1997).

Moline et al., "Postpartum Depression: A Guide for Patients and Families," Expert Consensus Guidelines Series—Treatment of Depression in Woman,112-113 (2001).

Mondeshka et al., "Racemische und optisch active 2-Chlorethylcarbamoyl-Derivate des 7,8-Dimethoxy-1-phenyl-1*H*-3-benzazepins: Neue Strukturtypen von DA, NE und 5-HT Uptake Inhibitoren," Arch. Pharm., 323:829-832 (1990).

Morgan et al., "Pharmacokinetics Properties, Metabolism and Tolerability of Lorcaserin in Healthy Volunteers," presented at the Obesity Society, (2008).

Morisette et al., "High-throughput crystallization: polymorphs, salts, co-crystals and solcates of pharmaceutical solids," Advanced Drug Delivery Reviews 56(3):275-300 (2004).

Morrow: "Insurers Find Small Gains in Weight Control With Belviq", Managed Care, vol. 21, No. 8, Aug. 1, 2012, pp. 45-46.

Muller et al., "Intracellular 5-HT2C-Receptor Dephosphorylation: A New Target for Treating Drug Addiction," Trends in Pharmacological Sciences, 27(9):455-58 (2006).

Nagase et al., "An Anhydrous Polymorphic Form of Trehalose," Carbohydrate Research 337(2):167-173 (2002).

Nagle et al., "Efficient Synthesis of β-amino Bromides," Tetrahedron Letters, 41:3011-4 (2000).

Nair et al., "Preparation of 2,3,4,5-Tetrahydro-3,1 H-benzazepine-2-one," Indian J. Chem., 5:169-70 (1967).

National Institute on Drug Abuse, Proc. 41st Ann. Scientific Mtg. 356-401 (1979).

Navarro-Vazquez et al., "A Study of Aryl Radical Cyclization in Enaminone Esters," J. Org. Chem., 67:3213-20 (2002).

Neumeyer et al., "Development of a High Affinity and Stereoselective Photoaffinity Label for the D-1 Dopamine Receptor: Synthesis and Resolution of 7-[125I]Iodo-8-hydroxy-3-methyl-1-(4'-azidophenyl)-2,3,4,5-tetrahydro-1H-3-benzazepine," J. Med. Chem., 33(2):521-6 (1990).

Niendam et al., "Neurocognitive Performance and Functional Disability in the Psychosis Prodrome," Schizophrenia Research, 84:100-111 (2006).

Ohnmacht et al., "Naphtho[2,1-b][1,5]-and [1,2-f][1,4]oxazocines as Selective NK1 Antagonists," Biorganic & Medicinal Chem. 12(10):2653-2666 (2004).

Okuno et al., "Photocyclization of N-chloroacetyl-2,5-dimethoxyphenethylamine. Synthesis of Pyrroloindoles," Chem. Pharm. Bull., 23(11):2584-90 (1975).

O'Neil et al: "Randomized Placebo-Controlled Clinical Trial of Lorcaserin for Weight Loss in Type 2 Diabetes Mellitus: The BLOOM-DM Study", Obesity, vol. 20, No. 7, Jul. 1, 2012, pp. 1426-1436.

Orito et al., "Benzolactams-1: Alkylation of 1,2,4,5-Tetrahydro-3-Methyl-3H-3-Benzazepin-2-One With Sodium Hydride and Alkyl Halide," Tetrahedron 36:1017-1021 (1980).

Orito et al., "Total Synthesis of Pseudo Type of Protopine Alkaloids," Heterocycles, 14(1):11-14 (1980).

Orito, et al., "Synthetic Studies of Heterocyclic Compounds I. Alkylation and Acylation of 1,2,4,5- Tetrahydro-3-Methyl-3H-3-Benzazepin-2-one," CASREACT, 93:7990 (1979).

Orlistat Prescribing Information Jan. 2012.

Paulekuhn et al., "Trends in Active Pharmaceutical Ingredient Salt Selection Based on Analysis of The Orange Book Database." J. Med. Chem., 50(26):6665-6672 (2007).

Pauvert et al., "Silver Nitrate-Promoted Ring Enlargement of 1-tribromomethyl-1,2-dihydro- and 1- tribromethyl-1,2, 3,4-tetrahydro-isoquinoline Derivatives: Application to the Synthesis of the Antianginal Zatebradine," Tetrahedron Letters, 44:4203-6 (2003).

Pawan et al., "Preliminary Study on the Effects of Fenfluramine Derivative, 'S992' In Man," British Journal of Pharmacology, 41(2): 416P-417P (1971).

Pecherer et al., "The Synthesis of Some 7- and 7,8-Substituted 2,3,4,5-tetrahydro-1H-3-benzazepines," J. Het. Chem., 8(5):779-783 (1971).

Pecherer et al., "A Novel Synthesis of Aromatic Methoxy and Methylenedioxy Substituted 2,3,4,5- tetrahydro-1H-3-benzazepines," J. Het. Chem., 9:609-16 (1972).

Perry et al., "Prospective Study of Risk Factors for Development on Non-Insulin Dependent Diabetes in Middle Aged British Men," BMJ, 310:560-564 (1995).

Pfeiffer et al., "Dopaminergic Activity of Substituted 6-Chloro-1-phenyl-2,3,4,5-tetrahydro-1H-3- benzazepines," J. Med. Chem., 25(4):352-8 (1982).

Piesla et al., "Atypical Antipsychotic-Like Effects of 5-HT2C Agonists," Schizophrenia Research 49: 95 (2001).

Porras, et al., "5-HT2A and 5-HT2C/2B Receptor Subtypes Modulate Dopamine Release Induced in Vivo by Amphetamine and Morphine in Both the Rat Nucleus Accumbens and Striatum," Neuropsychopharmacology 26: 311-324 (2002).

Prous Science Integrity entry 156186, 2007.

Prous Science Integrity entry 354056, 2007.

Remington's Pharmaceutical Sciences 17th ed., Mack Publishing Company, Easton Pa.: xv-xvi, 1409-1423 (1985).

Rosenzweig-Lipson et al., "Vabicaserin: Effects of a Novel 5HT2C Agaonist on Medial Prefrontal Cortex Neurotransmission, Cognition and Sensorimotor Gating," 29th ECNP Congress, Vienna, Austria (2007).

Roth et al., "Anorectic Efficacy of the Fenfluramine/Phentermine Combination in Rats: Additivity or Synergy?" Eur. J. Pharmacol., 373(2-3):127-34 (1999).

Rothman et al., "Evidence of Possible Involvement of 5-HT2B Receptors in the Cardiac Valvulopathy Associated with Fenfluramine and Other Serotonergic Medications," Circulation, 2836-41 (2000).

Rothman, "Treatment of Alcohol and Cocaine Addiction by the Combination of Pemoline and Fenfluramine: A Preliminary Case Series," Journal of Substance Abuse Treatment, 12(6):449-53 (1995).

Rowland et al., "Acute Anorectic Effect of Single and Combined Drugs in Mice Using a Non-deprivation Protocol," Psychopharmacology (Berl), 157(2):193-6 (2001).

Rowland et al., "Anorectic Effect of Dehydroepiandrosterone Combined with Dexfenfluramine or Thionisoxetine," Eur. J. Pharmacol., 419(1):61-4 (2001).

Rowland et al., "Comparison of Either Norepinephrine-uptake Inhibitors or Phentermine Combined with Serotonergic Agents on Food Intake in Rats," Psychopharmacology (Berl), 149(1):77-83 (2000).

Rowland et al., "Effects of the Cannabinoid Receptor Antagonist SR 141716, Alone and in Combination with Dexfenfluramine or Naloxone, on Food Intake in Rats," Psychopharmacology (Berl), 159(1):111-6 (2001).

Sadeque et al., "Formation Kinetics of Lorcaserin Sulfamate," presented at N. American ISSX (2008).

Sadeque, et al. "Formation Kinetics of Lorcaserin Sulfamate." Drug Metab Rev 2008, 40(Suppl. 3): Abst 95.

Schaffner et al., "Preventing Severe Mental Illnesses—New Prospects and Ethical Challenges," Schizophrenia Research, 51:3-15 (2001).

Schlademan et al., "Synthesis of Oxo- and 1-Hydroxy-azobenzocycloalkanes," J. Chem. Soc. Perkin Trans., 2:213-215 (1972).

Serajuddin et al., "Salt formation to improve drug solubility," Advanced Drug Delivery Reviews 59(7):603-616 (2007).

Sibutramine Prescribing Information Aug. 2012.

(56) References Cited

OTHER PUBLICATIONS

Silverstone, "Appetite Suppressants: a Review." Drugs. 43:6, (1992). Abstract.

Smith et al., "Discovery and SAR of New Benzazepines as Potent and Selective 5HT2c Receptor Agonists for the Treatment of Obesity," Bioorganic & Medicinal Chemistry Letters, 15(5):1467-1470 (2005).

Smith et al., "Lorcaserin (APD356), a Selective 5-HT2c Agonist, Safely Induces Weight-Loss in a 12 Week Study of Healthy Obese Patients," presented at American Diabetes Association (2006).

Smith et al., "APD-356, An Orally-Active Selective 5HT2c Agonist, Reduces Body Weight in Obese Adult Men and Women," Diabetes 55 [Supp/1]:80 (2006).

Smith et al., "Effect of APD356, a Selective 5-HT2c Agonist, on Weight Loss in a 4 Week Study of Healthy Obese Patients," presented at the Annual North American Association for the Study of Obesity, (2005).

Smith et al: "Multicenter, Placebo-Controlled Trial of Lorcaserin for Weight Management.", New England Journal of Medicine, vol. 3, No. 36, Jul. 15, 2015, pp. 35-46.

Smith, "5-HT2C Receptor Agonists for the Treatment of Obesity," Presentation, Arena Pharmaceuticals, Inc., Jul. 28, 2010, 30 pages.

Smith, "Discovery of Lorcaserin (APD356): A Selective 5HT2C Agonist for the Treatment of Obesity," Presentation, Arena Pharmaceuticals, Inc., (2006).

Smith, et al, Discovery and structure—activity relationship of (1R)-8-chloro-2,3,4,5-tetrahydro-1-methyl-1 H-3-benzazepine (lorcaserin), in a selective serotonin 5-HT2c receptor agonist for the treatment of obesity, retreived from the internet on Dec. 21, 2007 <URL:http:pubs.acs.org/journals/jmcmar/index.html>.

Smith, et al., "Discovery and Structure—Activity Relationship of (1R)-8-Chloro-2,3,4,5-tetrahydro-1-methyl-1 H-3-benzazepine (Lorcaserin), a Selective Serotonin 5-HT2c Receptor Agonist for the Treatment of Obesity," J. Med. Chem. 51:305-313 (2008).

Sussman et al., "Effects of Nefazodone on Body Weight: A Pooled Analysis of Selective Serotonin Reuptake Inhibitor- and Imipramine-Controlled Trails," J. Clin. Psychiatry, 62:4:256-60 (2001).

Tecott et al., "Eating Disorder and Epilepsy in Mice Lacking 5-HT2C Serotonin Receptors." Nature, 374:542-546 (1996).

Tietze et al., "Efficient Synthesis of 2, 3, 4, 5-Tetrahydro-1 H-3-Benzazepines by Intramolecular Heck Reaction," Synthesis, 876-880 (1993).

Tohda et al., "Molecular Pathopharmacology of 5-HT2C Receptors and the RNA Editing in the Brain." J. Pharma. Science, 100: 427-432 (2006).

Tsuang et al., "Towards the Prevention of Schizophrenia," Biol. Psychiatry, 48:349-356 (2000).

Usmani et al., "Identification of Human Liver Cytochrome P450 isoforms Involved in the Metabolism of Lorcaserin," presented at N. American ISSX (2008).

Usmani, et al. "Identification of Human Liver Cytochrome P450 Isoforms Involved in the Metabolism of Lorcaserin," Drug Metab Rev 2008, 40(Suppl. 3): Abst 273.

Van Oekelen et al., "5-HT2A and 5-HT2C Receptors and Their Atypical Regulation Properties," Life Sciences, 72:2429-2449 (2003).

Vanderlaan et al., "Synthesis and Oxidative Coupling of (±)-3-Sxoreticuline," J. Org. Chem., 50 (6) :743-7 (1985).

Vink et al., "Risk Factors for Anxiety and Depression in the Elderly: A Review," J. Affect. Disord., 106:29-44 (2008).

Wang et al. "The use of lorcaserin in the management of obesity: a critical appraisal." Drug Design, Devel. & Therapy (Dec. 1, 2010).

Wang et al: "Lorcaserin Hydrochloride", Drugs of the Future, vol. 32, No. 9, Jan. 1, 2007, p. 766.

Wang et al: "The Use of Lorcaserin in the Management of Obesity: A Critical Appraisal", Drug Design, Development and Therapy, Dec. 1, 2010, p. 1.

Wang, et al. "Lorcaserin hydrochloride." Drugs of the Future vol. 32:9 (Jan. 1, 2007) p. 766.

Webb, "APD356, A Potential New Treatment for Obesity," Presentation, Arena Pharmaceuticals, Inc., Aug. 11, 2005, 43 pages.

Weinstock et al., "Separation of Potent Central and Renal Dopamine Agonist Activity in Substituted 6-Chloro-2,3,4,5-tetrahydro-7,8-dihydroxy-1-phenyl-1H-3-benzazepines," J. Med. Chem., 23(9):973-5 (1980).

Wellman et al., "Synergistic Interactions Between Fenfluramine and Phentermine," Int. J. Obes., 23(7):723-4 (1999).

Wilk, "Exchange Type Reactions Between Oxiranes or Thiiranes and 2-Hydroxyalkyl or 2-Thioalkyl Amines and Sulfides," Pol. J. Chem. 62:895 (1988).

Williams, Chemistry Demystified, pp. 123, 126 (2003).

Winkler, "Obesity and Hemostasis" Archives of Gynecology & Obst. 261(1):25-29 (1997).

Wise, "Addiction Becomes a Brain Disease," Neuron, 26: 27-33 (2000).

Wisner et al., "Postpartum Depression," N. Engl. J. Med., 347(3):194-199 (2002).

Woods et al., "Annual Report: Evaluation of New Compounds for Opoid Activity," National Institute on Drug Abuse, Proceedings of the 41st Annual Scientific Meeting pp. 356-401 (1979).

Wu et al., "Amino Diol Based Asymmetric Syntheses of a Fused Benzazepine as a Selective D1 Dopamine Receptor," Organic Process Research & Development, 1(5):359-64 (1997).

Xu et al., "In Vivo Metabolism of Lorcaserin in Preclinical Species," presented at N. American ISSX (2008).

Xu, et al., "In Vivo Metabolism of Lorcaserin, A Novel Selective Serotonin 5-HT2C Receptor Agonist, in Preclinical Species." Drug Metab Rev 2008, 40(Suppl. 3): Abst 310.

Yasuda et al., "A Novel and Stereoselective Synthesis of (±)-Cephalotaxine and its Analogue," Tetrahedron Letters, 27(18):2023-6 (1986).

Yonemitsu et al., "Photolysis of N-Chloracetyl-O-methyl-L-tyrosine to an Azaazulene," J. Am. Chem. Soc.,, 89(4): 1039-40 (1967).

Yonemitsu et al., "Photocyclization of Pharmacodynamic Amines. IV. Novel Heterocycles from N-chloroacetyl-3,4-dimethoxyphenethylamine," J. Am. Chem. Soc., 92(19):5686-90 (1970).

Yonemitsu et al., "Photocyclization of Pharmodynamic Amines. II. X-Ray Analysis of a Noncentrosymmetric Tetracyclic Indole," J. Am. Chem. Soc., 90(23):6522-3 (1968).

Yonemitsu et al., "Photocyclizations of Tyrosines, Tyramines, Catecholamines, and Normescaline," J. Am. Chem. Soc., 90(3):776-84 (1968).

Yoshinaga et al., "Prevention of Mildly Overweight Children from Development of More Overweight Condition," Prevention Medicine, 38:172-174 (2004).

Zhang et al., "Convolutamines A-E, Novel β-Phenylethylamine Alkaloids from Marine Bryozoan Amathia convolute," Chem. Lett., 12:2271-2274 (1994).

"Clinical guidelines on the identification, evaluation, treatment of overweight and obesity in adults—the evidence report," National Institutes of Health. Obes Res1998;6(Suppl 2):51S-209S.

American Diabetes Association,"Position statement: Standards of medical care in diabetes—2013," Diabetes Care 2013;36(Suppl 1):S11-S66.

Caterson et al., "Maintained intentional weight loss reduces cardiovascular outcomes: Results from the Sibutramine Cardiovascular OUTcomes (SCOUT) trial," Diabetes Obes Metab 2012;14:523-530.

Elfhag et al., "Who succeeds in maintaining weight loss? A conceptual review of factors associated with weight loss maintenance and weight regain,"Obes Rev 2005;6:67-85.

FDA Briefing Document: Lorcaserin Hydrochloride, FDA Advisory Committee Meeting (Apr. 6, 2012).

Finer et al., "Prediction of response to sibutraminetherapy in obese non-diabetic and diabetic patients," Diabetes Obes Metab 2006;8:206-213.

Grundy et al."Diagnosis and management of the metabolic syndrome: An American Heart Association/National Heart, Lung, and Blood Institute scientific statement," Circulation 2005;112:2735-275.

(56) References Cited

OTHER PUBLICATIONS

Handjieva-Darlenska et al., "Initial weight loss on an800-kcal diet as a predictor of weight loss success after 8 weeks: The Diogenes study," Eur J Clin Nutr 2010;64:994-999.

James et al., "Effect of sibutramine on cardiovascular outcomes in overweight and obese subjects," N Engl J Med 2010;363: 905-917.

Knowler et al. "10-year follow-up of diabetesincidence and weight loss in the Diabetes Prevention Program Outcomes Study," Lancet 2009;374:1677-1686.

Knowler et al. "Reduction in the incidence of type 2 diabetes with lifestyle intervention or metformin," N Engl J Med 2002;346: 393-403.

Lyznicki et al. "Obesity: Assessment and management in primary care," Council on Scientific Affairs AMA. Am Fam Physician 2001;63:2185-2196.

Mechanick et al.,"American Association of Clinical Endocrinologists' position statement on obesity and obesity medicine," Endocr Pract 2013;18:642-648.

O'Meara et al., "A rapid and systematic review of the clinical effectiveness and cost-effectiveness of orlistat in the management of obesity," Health Technol Assess 2001;5:1-81.

O'Neil et al., "Early weight loss with naltrexone SR/bupropionSR combination therapy for obesity predicts long-term weight loss (Abstract)," Obesity 2009;17:S109.

Poirier et al."Obesity and cardiovascular disease: Pathophysiology, evaluation, and effect of weight loss: An update of the 1997 American Heart Association Scientific Statement on Obesity and Heart Disease From the Obesity Committee of the Council on Nutrition, Physical Activity, and Metabolism," Circulation 2006;113:898-918.

Rissanen et al., "Predictive value of earlyweight loss in obesity management with orlistat: An evidence-based assessment of prescribing guidelines," Int J Obes Relat Metab Disord 2003;27:103-109.

Smith et al., "Early Weight Loss While on Lorcaserin, Diet, and Exercise as a Predictor of Week 52 Weight-Loss Outcomes," Obesity (2014) 00, 00-00. doi:10.1002/oby.20841.

Stotland et al., "Early treatment response as a predictor of ongoingweight loss in obesity treatment," Br J Health Psychol 2005;10:601-614.

Wadden et al., "Clinical correlates of short- and long-term weight loss," Am J Clin Nutr 1992;56(Suppl 1):271S-274S.

\* cited by examiner

METHOD OF WEIGHT MANAGEMENT

CROSS-REFERENCE TO RELATED APPLICATIONS

This application is a continuation of U.S. patent application Ser. No. 14/002,235, filed Aug. 29, 2013, which is a National Stage Entry of International Patent Application No. PCT/US12/63711, filed Nov. 6, 2012, and claims the benefit under 35 U.S.C. §119(e) of U.S. Provisional Ser. No. 61/711,413, filed Oct. 9, 2012, the contents of which are incorporated by reference in their entirety into the current disclosure.

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also the decrease in activity in most people's lives. Currently about 30% of the population of the USA is now considered obese.

Whether someone is classified as overweight or obese is generally determined on the basis of their body mass index (BMI) which is calculated by dividing body weight (kg) by height squared (m²). Thus, the units of BMI are kg/m² and it is possible to calculate the BMI range associated with minimum mortality in each decade of life. Overweight is defined as a BMI in the range 25-30 kg/m², and obesity as a BMI greater than 30 kg/m² (see table below).

| \multicolumn{2}{c}{CLASSIFICATION OF WEIGHT BY BODY MASS INDEX (BMI)} ||
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. The strength of the link between obesity and specific conditions varies. One of the strongest is the link with type 2 diabetes. Excess body fat underlies 64% of cases of diabetes in men and 77% of cases in women (Seidell, Semin Vasc Med 5:3-14 (2005)). Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I. J., et al., BMJ 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have been launched in the USA and Europe: Orlistat (Xenical™), a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT is believed to work by inducing a feeling of satiety, such that a subject with enhanced 5-HT stops eating earlier and fewer calories are consumed. It has been shown that a stimulatory action of 5-HT on the 5-HT$_{2C}$ receptor plays an important role in the control of eating and in the anti-obesity effect of d-fenfluramine. As the 5-HT$_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective 5-HT$_{2C}$ receptor agonist can be a more effective and safe anti-obesity agent. Also, 5-HT$_{2C}$ knockout mice are overweight with cognitive impairment and susceptibility to seizure.

It is believed that the 5-HT$_{2C}$ receptor may play a role in obsessive compulsive disorder, some forms of depression, and epilepsy. Accordingly, agonists can have anti-panic properties, and properties useful for the treatment of sexual dysfunction.

In sum, the 5-HT$_{2C}$ receptor is a receptor target for the treatment of obesity and psychiatric disorders, and it can be seen that there is a need for selective 5-HT$_{2C}$ agonists which safely decrease food intake and body weight.

Compounds and formulations presented herein can comprise the selective 5-HT$_{2C}$-receptor agonist (R)-8-chloro-1-methyl-2,3,4,5-tetrahydro-1H-3-benzazepine (Compound 1), and are useful for, inter alia, weight management, including weight loss and the maintenance of weight loss. Compound 1 is disclosed in PCT patent publication WO2003/086303, which is incorporated herein by reference in its entirety.

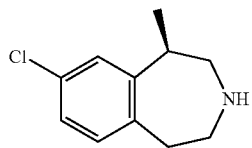

Various synthetic routes to (R)-8-chloro-1-methyl-2,3,4,5-tetrahydro-1H-3-benzazepine, its related salts, enantiomers, crystalline forms, and intermediates, have been reported in WO 2005/019179, WO 2006/069363, WO 2007/120517, WO 2008/070111, and WO 2009/111004 each of which is incorporated herein by reference in its entirety.

Combinations of (R)-8-Chloro-1-methyl-2,3,4,5-tetrahydro-1H-3-benzazepine with other agents, including without limitation, phentermine, and uses of such combinations in therapy are described in WO 2006/071740, which is incorporated herein by reference in its entirety.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In December 2009, Arena Pharmaceuticals submitted a New Drug Application, or NDA, for lorcaserin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

There exists a need for safely treating individuals who are in need of treatment with lorcaserin. The present disclosure satisfies this need and provides related advantages as well.

SUMMARY

Provided is a method of determining if an individual is a responder to treatment with (R)-8-chloro-1-methyl-2,3,4,5-tetrahydro-1H-3-benzazepine or a pharmaceutically acceptable salt, solvate or hydrate thereof, comprising the steps of:

measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual, wherein if the individual has achieved a threshold effect after said first time period of administration, the individual is a responder.

Also provided is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising:

measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual; and selecting the individual for treatment with (R)-8-chloro-1-methyl-2,3,4,5-tetrahydro-1H-3-benzazepine or a pharmaceutically acceptable salt, solvate or hydrate thereof if the individual has achieved a threshold effect after said first time period of administration.

Also provided is a method for weight management in an individual in need thereof, comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any one of the methods described herein.

Also provided is a method for weight management in an individual in need thereof, comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to any one of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a method for decreasing food intake in an individual in need thereof, comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any one of the methods described herein.

Also provided is a method for decreasing food intake in an individual in need thereof, comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to the method of any one of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a method for inducing satiety in an individual in need thereof, comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any one of the methods described herein.

Also provided is a method for inducing satiety in an individual in need thereof, comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to the method of any one of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a method for the treatment of obesity in an individual in need thereof, comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any one of the methods described herein.

Also provided is a method for the treatment of obesity in an individual in need thereof, comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to the method of any one of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a method for the prevention of obesity in an individual in need thereof, comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to a responder or selected for treatment according to any one of the methods described herein.

Also provided is a method for the prevention of obesity in an individual in need thereof, comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to any one of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a compound for use in any of the methods described herein.

Also provided is a composition for use in a method of weight management in an individual, comprising a therapeutically effective amount of (R)-8-chloro-1-methyl-2,3,4,5-tetrahydro-1H-3-benzazepine or a pharmaceutically acceptable salt, solvate or hydrate thereof;

wherein the individual has previously been determined to be a responder or selected for treatment according to any one of the methods described herein.

Also provided is a kit for use in a method of weight management in an individual, comprising a therapeutically effective amount of (R)-8-chloro-1-methyl-2,3,4,5-tetrahydro-1H-3-benzazepine or a pharmaceutically acceptable salt, solvate or hydrate thereof; and instructions indicating that the (R)-8-chloro-1-methyl-2,3,4,5-tetrahydro-1H-3-benzazepine or a pharmaceutically acceptable salt, solvate or hydrate thereof is to be administered to an individual who has previously been determined to a responder or selected for treatment according to any one of the methods described herein.

BRIEF DESCRIPTION OF FIGURES

FIG. 2 shows weight loss through Week 52 for Week 12 responders and non-responder with and without diabetes.

DETAILED DESCRIPTION

Figure 1:
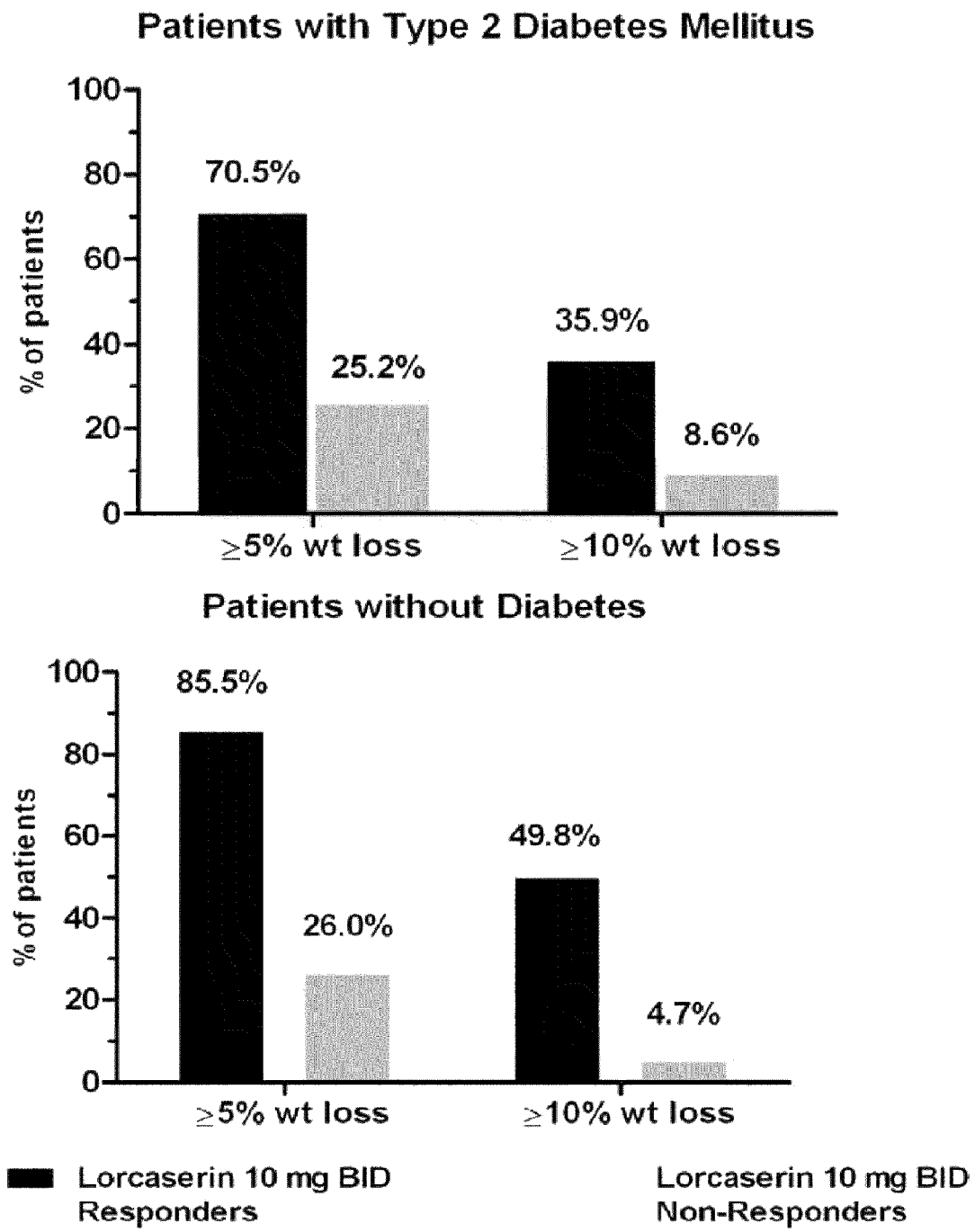
FIG. 1 provides data for the percentage of patients achieving ≥5% weight loss or ≥10% weight at 52 weeks for both responders and non-responders. The top panel is for patients with type 2 diabetes mellitus. The bottom panel is for patients without type 2 diabetes mellitus.

As used in the present specification, the following words and phrases are generally intended to have the meanings as set forth below, except to the extent that the context in which they are used indicates otherwise.

INDIVIDUAL: As used herein, an "individual" is a human. An individual can be an adult or prepubertal (a child) and can be of any gender. The individual can be a patient or other individual seeking treatment. The methods disclosed herein can also apply to non-human mammals such as livestock or pets.

Plurality of Individuals: As used herein, a "plurality of individuals" means more than one individual.

ADMINISTERING: As used herein, "administering" means to provide a compound or other therapy, remedy or treatment. For example, a health care practitioner can directly provide a compound to an individual in the form of a sample, or can indirectly provide a compound to an individual by providing an oral or written prescription for the compound. Also, for example, an individual can obtain a compound by themselves without the involvement of a health care practitioner. Administration of the compound may or may not involve the individual actually internalizing the compound. In the case where an individual internalizes the compound the body is transformed by the compound in some way.

PRESCRIBING: As used herein, "prescribing" means to order, authorize or recommend the use of a drug or other therapy, remedy or treatment. In some embodiments, a health care practitioner can orally advise, recommend or authorize the use of a compound, dosage regimen or other treatment to an individual. In this case the health care practitioner may or may not provide a prescription for the compound, dosage regimen or treatment. Further, the health care practitioner may or may not provide the recommended compound or treatment. For example, the health care practitioner can advise the individual where to obtain the compound without providing the compound. In some embodiments, a health care practitioner can provide a prescription for the compound, dosage regimen or treatment to the individual. For example, a health care practitioner can give a written or oral prescription to an individual. A prescription can be written on paper or on electronic media such as a computer file, for example, on a hand held computer device. For example, a health care practitioner can transform a piece of paper or electronic media with a prescription for a compound, dosage regimen or treatment. In addition, a prescription can be called in (oral) or faxed in (written) to a pharmacy or a dispensary. In some embodiments, a sample of the compound or treatment can be given to the individual. As used herein, giving a sample of a compound constitutes an implicit prescription for the compound. Different health care systems around the world use different methods for prescribing and administering compounds or treatments and these methods are encompassed by the disclosure.

A prescription can include, for example, an individual's name and/or identifying information such as date of birth. In addition, for example, a prescription can include, the medication name, medication strength, dose, frequency of administration, route of administration, number or amount to be discpensed, number of refills, physician name, physician signature. Further, for example, a prescription can include a DEA number or state number.

A healthcare practitioner can include, for example, a physician, nurse, nurse practitioner or other related health care professional who can prescribe or administer compounds (drugs) for weight management. In addition, a healthcare practitioner can include anyone who can recommend, prescribe, administer or prevent an individual from receiving a compound or drug including, for example, an insurance provider.

PREVENT, PREVENTING, OR PREVENTION: As used herein, the term "prevent," "preventing" or "prevention" such as prevention of obesity means prevention of the occurrence or onset of one or more symptoms associated with a particular disorder and does not necessarily mean the complete prevention of a disorder. For example, the term "prevent," "preventing" and "prevention" refers to the administration of therapy on a prophylactic or preventative basis to an individual who may ultimately manifest at least one symptom of a disease or condition but who has not yet done so. Such individuals can be identified on the basis of risk factors that are known to correlate with the subsequent occurrence of the disease. Alternatively, prevention therapy can be administered without prior identification of a risk factor, as a prophylactic measure. Delaying the onset of the at least one symptom can also be considered prevention or prophylaxis.

TREAT, TREATING, OR TREATMENT: As used herein the term "treat," "treating" or "treatment" refers to the administration of therapy to an individual who already manifests at least one symptom of a disease or condition or who has previously manifested at least one symptom of a disease or condition. For example, "treating" can include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylacticly and/or therapeutically. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. For example, a method for treatment of obesity can result in weight loss; however, the weight loss does not need to be enough such that the individual is no longer obese. It has been shown that even modest decreases in weight or related parameters such as BMI, waist circumference and percent body fat, can result in improvement of health, for example, lower blood pressure, improved blood lipid profiles, or a reduction in sleep apnea.

WEIGHT MANAGEMENT: As used herein, the term "weight management" means controlling body weight and in the context of the present disclosure is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight. Maintenance of weight loss (weight maintenance) includes preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weigh gained after weight loss, controlling weight gain after weight loss or slowing the rate of weight gain after weight loss. As used herein, "weight management in an individual in need thereof" refers to a judgment made by a healthcare practitioner that an individual requires or will benefit from weight management treatment. This judgment is made based on a variety of factors that are in the realm of a healthcare practitioner's expertise, but that includes the knowledge that the individual has a condition that is treatable by the methods disclosed herein.

DECREASING FOOD INTAKE: As used herein, "decreasing food intake in an individual in need thereof" refers to a judgment made by a healthcare practitioner that an individual requires or will benefit from decreasing food intake. This judgment is made based on a variety of factors that are in the realm of a healthcare practitioner's expertise, but that includes the knowledge that the individual has a condition, for example, obesity, that is treatable by the methods disclosed herein. In some embodiments, an individual in need of decreasing food intake is an individual who is overweight. In some embodiments, an individual in need of decreasing food intake is an individual who is obese.

SATIETY: As used herein, "satiety" is the quality or state of being fed or gratified to or beyond capacity. Satiety is a feeling that an individual has and so it is often determined by asking the individual, orally or in writing, if they feel full, sated, or satisfied at timed intervals during a meal. For example, an individual who feels sated may report feeling full, feeling a decreased or absent hunger, feeling a decreased or absent desire to eat, or feeling a lack of drive to eat. While fullness is a physical sensation, satiety is a mental feeling. An individual who feels full, sated or satisfied is more likely to stop eating and therefore inducing satiety can result in a decrease in food intake in an individual. As used herein, "inducing satiety in an individual in need thereof" refers to a judgment made by a healthcare practitioner that an individual requires or will benefit from inducing satiety. This judgment is made based on a variety of factors that are in the realm of a healthcare practitioner's expertise, but that includes the knowledge that the individual has a condition, for example, obesity, that is treatable by the methods of the disclosure.

TREATMENT OF OBESITY: As used herein, "treatment of obesity in an individual in need thereof" refers to a judgment made by a healthcare practitioner that an individual requires or will benefit from treatment of obesity. This judgment is made based on a variety of factors that are in the realm of a healthcare practitioner's expertise, but that includes the knowledge that the individual has a condition that is treatable by the methods of the disclosure. To determine whether an individual is obese one can determine a body weight, a body mass index (BMI), a waist circumference or a body fat percentage of the individual to determine if the individual meets a body weight threshold, a BMI threshold, a waist circumference threshold or a body fat percentage threshold.

PREVENTION OF OBESITY: As used herein, "prevention of obesity in an individual in need thereof" refers to a judgment made by a healthcare practitioner that an individual requires or will benefit from prevention of obesity. This judgment is made based on a variety of factors that are in the realm of a healthcare practitioner's expertise, but that includes the knowledge that the individual has a condition that is treatable by the methods disclosed herein. In some embodiments, an individual in need of prevention of obesity is an individual who is overweight (also called pre-obese). In some embodiments, an individual in need of prevention of obesity is an individual who has a family history of obesity. To determine whether an individual is overweight one can determine a body weight, a body mass index (BMI), a waist circumference or a body fat percentage of the individual to determine if the individual meets a body weight threshold, a BMI threshold, a waist circumference threshold or a body fat percentage threshold.

ADVERSE EVENT OR TOXIC EVENT: As used herein, an "adverse event" or "toxic event" is any untoward medical occurrence that may present itself during treatment. Adverse events associated with treatment with Compound 1 or a pharmaceutically acceptable salt, solvate or hydrate thereof include, for example, abdominal pain, diarrhea, dyspepsia, stomach discomfort, and worsening renal impairment, dizziness, headache. Other possible adverse effects based on observations from studies in monkeys include emesis, decreased food intake, weight loss, decreased activity, spontaneous penile erection, tremors or seizures. Additional possible adverse effects include, for example, nausea, blurred vision, paresthesias, dry mouth and fatigue. In the methods disclosed herein, the term adverse event can be replaced by other more general terms such as toxicity. The term "reducing the risk" of an adverse event means reducing the probability that an adverse event or toxic event could occur.

As used herein, the term "phentermine" refers to 1,1-dimethyl-2-phenyl-ethylamine, including phentermine derivatives and pharmaceutically acceptable salts thereof, such as, but not limited to, chlorphentermine (2-(4-chloro-phenyl)-1,1-dimethyl-ethylamine) and the like. In one embodiment, phentermine is in the HCl salt form of 1,1-dimethyl-2-phenyl-ethylamine.

As used herein, the term "greater than" is used interchangeably with the symbol > and the term less than is used interchangeably with the symbol <. Likewise the term less than or equal to is interchangeably with the symbol ≤.

When an integer is used in a method disclosed herein, the term "about" can be inserted before the integer. For example, the term "greater than 29 kg/m$^2$" can be substituted with "greater than about 29 kg/m$^2$".

As used in the present specification, the following abbreviations are generally intended to have the meanings as set forth below, except to the extent that the context in which they are used indicates otherwise.

| | |
|---|---|
| ° C. | Degrees Celsius |
| A1C | Glycated hemoglobin |
| AUC | Area under curve |
| BID | Twice a day |
| BL | Baseline |
| BMI | Body Mass Index |
| BP | Blood pressure |
| BPM/bpm | Beats per minute |
| CI | Confidence interval |
| cm | Centimeter |
| DBP | Diastolic blood pressure |
| DEA | Drug Enforcement Administration |
| dL | Deciliter |
| DMH | Dorsomedial hypothalamic nucleus |
| DSC | Differential scanning calorimetry |
| eq. | equivalents |
| FDA | Food and Drug Administration |
| FPG | Fasting Plasma Glucose |
| IFG | Impaired Fasting Glucose |
| g | Gram |
| h | Hour |
| HDL | High-density lipoprotein |
| Kg/kg | Kilogram |
| lbs | Pounds |
| LDL | Low-density lipoprotein |
| M | Molar |
| m$^2$ | Square Meter |
| mg | Milligram |
| min | Minute |
| MITT | Modified intention to treat |
| LOCF | Last observation carried forward |

| | -continued |
|---|---|
| mmHg | Millimeters of Mercury |
| N | Number |
| NDA | New Drug Application |
| PVN | Paraventricular hypothalamic nucleus |
| QD | Once a day |
| ROCC | Receiver operating characteristic curve |
| SBP | Systolic blood pressure |
| T2DM | Type-two Diabetes Mellitus |
| TGA | Thermogravimetric Analysis |
| W12 | Week 12 |
| W52 | Week 52 |
| wt | Weight |
| XRPD | X-ray powder diffraction |

Throughout this specification, unless the context requires otherwise, the word "comprise", or variations such as "comprises" or "comprising" will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied *mutatis mutandis* to each and every other embodiment unless specifically stated otherwise.

Those skilled in the art will appreciate that the invention(s) described herein is susceptible to variations and modifications other than those specifically described. It is to be understood that the invention(s) includes all such variations and modifications. The invention(s) also includes all of the steps, features, compositions and compounds referred to or indicated in this specification, individually or collectively, and any and all combinations or any two or more of said steps or features unless specifically stated otherwise.

The present invention(s) is not to be limited in scope by the specific embodiments described herein, which are intended for the purpose of exemplification only. Functionally-equivalent products, compositions and methods are clearly within the scope of the invention(s), as described herein.

It is appreciated that certain features of the invention(s), which are, for clarity, described in the context of separate embodiments, can also be provided in combination in a single embodiment. Conversely, various features of the invention(s), which are, for brevity, described in the context of a single embodiment, can also be provided separately or in any suitable subcombination. For example, a method that recites prescribing or administering (R)-8-chloro-1-methyl-2,3,4,5-tetrahydro-1,1-3-benzazepine can be separated into two methods; one reciting prescribing (R)-8-chloro-1-methyl-2,3,4,5-tetrahydro-1H-3-benzazepine and the other reciting administering (R)-8-chloro-1-methyl-2,3,4,5-tetrahydro-1H-3-benzazepine. In addition, for example, a method that recites prescribing (R)-8-chloro-1-methyl-2,3,4,5-tetrahydro-1H-3-benzazepine and a separate method of the invention reciting administering (R)-8-chloro-1-methyl-2,3,4,5-tetrahydro-1H-3-benzazepine can be combined into a single method reciting prescribing and/or administering (R)-8-chloro-1-methyl-2,3,4,5-tetrahydro-1H-3-benzazepine.

Provided is a method of determining if an individual is a responder to treatment with (R)-8-chloro-1-methyl-2,3,4,5-tetrahydro-1H-3-benzazepine or a pharmaceutically acceptable salt, solvate or hydrate thereof, comprising the steps of:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual,
wherein if the individual has achieved a threshold effect after said first time period of administration, the individual is a responder.

Provided is a method of determining if an individual is a responder to treatment with (R)-8-chloro-1-methyl-2,3,4,5-tetrahydro-1H-3-benzazepine or a pharmaceutically acceptable salt, solvate or hydrate thereof, comprising the steps of:
administering (R)-8-chloro-1-methyl-2,3,4,5-tetrahydro-1H-3-benzazepine or a pharmaceutically acceptable salt, solvate or hydrate thereof to an individual for a first time period of administration;
measuring the individual's responsiveness to (R)-8-chloro-1-methyl-2,3,4,5-tetrahydro-1H-3-benzazepine or a pharmaceutically acceptable salt, solvate or hydrate thereof;
wherein if the individual has achieved a threshold effect after said first time period of administration, the individual is a responder.

Also provided is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual; and
selecting the individual for treatment with (R)-8-chloro-1-methyl-2,3,4,5-tetrahydro-1H-3-benzazepine or a pharmaceutically acceptable salt, solvate or hydrate thereof if the individual has achieved a threshold effect after said first time period of administration.

Also provided is a method for selecting an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising:
administering (R)-8-chloro-1-methyl-2,3,4,5-tetrahydro-1H-3-benzazepine or a pharmaceutically acceptable salt, solvate or hydrate thereof to an individual for a first time period of administration;
measuring the individual's responsiveness to (R)-8-chloro-1-methyl-2,3,4,5-tetrahydro-1H-3-benzazepine or a pharmaceutically acceptable salt, solvate or hydrate thereof; and
selecting the individual for treatment with (R)-8-chloro-1-methyl-2,3,4,5-tetrahydro-1H-3-benzazepine or a pharmaceutically acceptable salt, solvate or hydrate thereof if the individual has achieved a threshold effect after said first time period of administration.

Also provided is a method for assisting in the selection of an individual for treatment with (R)-8-chloro-1-methyl-2,3,4,5-tetrahydro-1H-3-benzazepine or a pharmaceutically acceptable salt, solvate or hydrate thereof from a plurality of individuals in need of weight management, comprising:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl- 2,3,4,5-tetrahydro-1H-3-benzazepine or a pharmaceutically acceptable salt, solvate or hydrate thereof to the individual, wherein if the measurement of the individual's responsiveness exceeds a threshold effect after said first time period of administration then the individual is suitable for prescription of a therapeutically effective amount of with (R)-8-chloro-1-methyl-2,3,4,5-tetrahydro-1H-3-benzazepine or a pharmaceutically acceptable salt, solvate or hydrate thereof.

In some embodiments, an individual in need of weight management is an individual who is overweight. In some embodiments, an individual in need of weight management is an individual who has excess visceral adiposity. In some embodiments, an individual in need of weight management is an individual who is obese. To determine whether an individual is overweight or obese one can determine a body weight, a body mass index (BMI), a waist circumference or a body fat percentage of the individual to determine if the individual meets a body weight threshold, a BMI threshold, a waist circumference threshold or a body fat percentage threshold.

Determination of body weight can be through the use of a visual estimation of body weight, the use of a weight measuring device, such as an electronic weight scale or a mechanical beam scale. In some embodiments, an individual in need of weight management is an adult male with a body weight greater than about 90 kg, greater than about 100 kg, or greater than about 110 kg. In some embodiments, an individual in need of weight management is an adult female with a body weight greater than about 80 kg, greater than about 90 kg, or greater than about 100 kg. In some embodiments, the individual is prepubertal and has a body weight greater than about 30 kg, greater than about 40 kg, or greater than about 50 kg.

The healthy range of BMI, and other measures of whether one is overweight or obese, can also be dependent on genetic or racial differences. For example, since Asian populations develop negative health consequences at a lower BMI than Caucasians, some nations have redefined obesity for their populations. For example, in Japan any BMI greater than 25 is defined as obese and in China any BMI greater than 28 is defined as obese. Similarly, different threshold values for body weight, waist circumference or body fat percentage can be used for different populations of individuals. The WHO recommends that countries should use all categories for reporting purposes with a view to facilitating international comparisons.

Determination of BMI can be through the use of a visual estimation of BMI, the use of a height measuring device such as a stadiometer or a height rod and the use of a weight measuring device, such as an electronic weight scale or a mechanical beam scale. In some embodiments, the individual in need of weight management is an adult with a BMI of greater than about 25 kg/m$^2$, greater than about 26 kg/m$^2$, greater than about 27 kg/m$^2$, greater than about 28 kg/m$^2$, greater than about 29 kg/m$^2$, greater than about 30 kg/m$^2$, greater than about 31 kg/m$^2$, greater than about 32 d kg/m$^2$, greater than about 33 kg/m$^2$, greater than about 34 kg/m$^2$, greater than about 35 kg/m$^2$, greater than about 36 kg/m$^2$, greater than about 37 kg/m$^2$, greater than about 38 kg/m$^2$, greater than about 39 kg/m$^2$, or greater than about 40 kg/m$^2$. In some embodiments, the individual is prepubertal with a BMI of greater than about 20 kg/m$^2$, greater than about 21 kg/m$^2$, greater than about 22 kg/m$^2$, greater than about 23 kg/m$^2$, greater than about 24 kg/m$^2$, greater than about 25 kg/m$^2$, greater than about 26 kg/m$^2$, greater than about 27 kg/m$^2$, greater than about 28 kg/m$^2$, greater than about 29 kg/m$^2$, greater than about 30 kg/m$^2$, greater than about 31 kg/m$^2$, greater than about 32 kg/m$^2$, greater than about 33 kg/m$^2$, greater than about 34 kg/m$^2$, or greater than about 35 kg/m$^2$.

Determination of waist circumference can be through the use of a visual estimation of waist circumference or the use of a waist circumference measuring device such as a tape measure.

Determinations of the healthy range of waist circumference and percentage body fat in an individual are dependent on gender. For example, women typically have smaller waist circumferences than men and so the waist circumference threshold for being overweight or obese is lower for a woman. In addition, women typically have a greater percentage of body fat than men and so the percentage body fat threshold for being overweight or obese for a woman is higher than for a man. Further, the healthy range of BMI and other measures of whether one is overweight or obese can be dependent on age. For example, the body weight threshold for considering whether one is overweight or obese is lower for a child (prepubertal individual) than for an adult.

In some embodiments, the individual in need of weight management is an adult male with a waist circumference of greater than about 100 cm, greater than about 110 cm, or greater than about 120 cm, or an adult female with a waist circumference of greater than about 80 cm, greater than about 90 cm, or greater than about 100 cm. In some embodiments, the individual is prepubertal with a waist circumference of about of greater than about 60 cm, greater than about 70 cm, or greater than about 80 cm.

Determination of body fat percentage can be through the use of a visual estimation of body fat percentage or the use of a body fat percentage measuring device such as bioelectric impedance, computed tomography, magnetic resonance imaging, near infrared interactance, dual energy X ray absorptiometry, use of ultrasonic waves, use of body average density measurement, use of skinfold methods, or use of height and circumference methods. In some embodiments, the individual in need of weight management is an adult male with a body fat percentage of greater than about 25%, greater than about 30%, or greater than about 35%, or an adult female with a body fat percentage of greater than about 30%, greater than about 35%, or greater than about 40%. In some embodiments, the individual is prepubertal with a body fat percentage of greater than about 30%, greater than about 35%, or greater than about 40%.

In some embodiments, the individual has an initial body mass index ≥25 kg/m$^2$.

In some embodiments, the individual has an initial body mass index ≥25 kg/m$^2$ and at least one weight related comorbid condition. In some embodiments, the weight related comorbid condition is selected from: hypertension, dyslipidemia, cardiovascular disease, glucose intolerance and sleep apnea. In some embodiments, the weight related comorbid condition is selected from: hypertension, dyslipidemia, and type 2 diabetes.

In some embodiments, the individual has an initial body mass index ≥27 kg/m$^2$. In some embodiments, the individual has an initial body mass index ≥27 kg/m$^2$ and at least one weight related comorbid condition. In some embodiments, the weight related comorbid condition is selected from: hypertension, dyslipidemia, cardiovascular disease, glucose intolerance and sleep apnea. In some embodiments, the weight related comorbid condition is selected from: hypertension, dyslipidemia, and type 2 diabetes.

In some embodiments, the individual has type 2 diabetes.

In some embodiments, the individual has impaired fasting glucose. In some embodiments, the individual has a fasting glucose of less than about 100 mg/dL. In some embodiments, the individual has a fasting glucose of less than about 70 mg/dL. In some embodiments, the individual has a fasting glucose of less than about 65 mg/dL. In some embodiments, the individual has a fasting glucose of less than about 50 mg/dL.

In some embodiments, the individual has an initial body mass index $\geq 30$ kg/m$^2$. In some embodiments, the individual has an initial body mass index $\geq 30$ kg/m$^2$ and at least one weight related comorbid condition. In some embodiments, the weight related comorbid condition is selected from: hypertension, dyslipidemia, cardiovascular disease, glucose intolerance and sleep apnea. In some embodiments, the weight related comorbid condition is selected from: hypertension, dyslipidemia, and type 2 diabetes.

In some embodiments, the first time period of administration is from about 2 weeks to about 6 months. In some embodiments, the first time period of administration is from about 4 weeks to about 4 months. In some embodiments, the first time period of administration is about 12 weeks.

In some embodiments, the threshold effect comprises a decrease in an assessment of weight.

In some embodiments, a decrease in an assessment of weight comprises weight loss of at least about 1%.

In some embodiments, a decrease in an assessment of weight comprises weight loss of at least about 1% and said first time period of administration is about 2 weeks. In some embodiments, a decrease in an assessment of weight comprises weight loss of at least about 1.5% and said first time period of administration is about 2 weeks.

In some embodiments, a decrease in an assessment of weight comprises weight loss of at least about 2%.

In some embodiments, a decrease in an assessment of weight comprises weight loss of at least about 2% and said first time period of administration is about 4 weeks. In some embodiments, a decrease in an assessment of weight comprises weight loss of at least about 2.5% and said first time period of administration is about 4 weeks.

In some embodiments, a decrease in an assessment of weight comprises weight loss of at least about 3%.

In some embodiments, a decrease in an assessment of weight comprises weight loss of at least about 3% and said first time period of administration is about 8 weeks. In some embodiments, a decrease in an assessment of weight comprises weight loss of at least about 3.5% and said first time period of administration is about 8 weeks. In some embodiments, a decrease in an assessment of weight comprises weight loss of at least about 3.9% and said first time period of administration is about 8 weeks.

In some embodiments, a decrease in an assessment of weight comprises weight loss of at least about 4%.

In some embodiments, a decrease in an assessment of weight comprises weight loss of at least about 4% and said first time period of administration is about 12 weeks. In some embodiments, a decrease in an assessment of weight comprises weight loss of at least about 4.5% and said first time period of administration is about 12 weeks. In some embodiments, a decrease in an assessment of weight comprises weight loss of at least about 4.6% and said first time period of administration is about 12 weeks.

In some embodiments, a decrease in an assessment of weight comprises weight loss of at least about 5%.

In some embodiments, a decrease in an assessment of weight comprises weight loss of at least about 5% and said first time period of administration is about 12 weeks.

In some embodiments, a decrease in an assessment of weight comprises weight loss of at least about 6%.

In some embodiments, a decrease in an assessment of weight comprises weight loss of at least about 6% and said first time period of administration is about 12 weeks. In some embodiments, a decrease in an assessment of weight comprises weight loss of at least about 6% and said first time period of administration is about 24 weeks. In some embodiments, a decrease in an assessment of weight comprises weight loss of at least about 6.1% and said first time period of administration is about 24 weeks. In some embodiments, a decrease in an assessment of weight comprises weight loss of at least about 5.9% and said first time period of administration is about 24 weeks.

In some embodiments, a decrease in an assessment of weight comprises weight loss of at least about 9%.

In some embodiments, a decrease in an assessment of weight comprises weight loss of at least about 8.5% and said first time period of administration is about 24 weeks. In some embodiments, a decrease in an assessment of weight comprises weight loss of at least about 9% and said first time period of administration is about 24 weeks.

In some embodiments, a decrease in an assessment of weight comprises a decrease in BMI.

In some embodiments, a decrease in an assessment of weight comprises a decrease in percent body fat.

In some embodiments, a decrease in an assessment of weight comprises a decrease in waist circumference.

In some embodiments, achievement of a threshold effect after the first time period of administration correlates with a likelihood of the individual achieving one or more additional beneficial effects after a second time period of administration.

In some embodiments, the second time period of administration is about one year.

In some embodiments, the one or more additional beneficial effects comprises an additional decrease in an assessment of weight.

In some embodiments, the one or more additional beneficial effects are chosen from a decrease in an assessment of weight, an improvement in cardiovascular indications and/or an improved glycemia.

In some embodiments, the one or more additional beneficial effects comprise a decrease in an assessment of weight. In some embodiments, the decrease in an assessment of weight comprises weight loss.

In some embodiments, the weight loss in an individual without type 2 diabetes is between about 10 and 12 kg. In some embodiments, the weight loss in an individual without type 2 diabetes is about 10 kg. In some embodiments, the weight loss in an individual without type 2 diabetes is about 10.5 kg.

In some embodiments, the weight loss in an individual with type 2 diabetes is at least about 5 kg. In some embodiments, the weight loss in an individual with type 2 diabetes is between about 5 and 10 kg. In some embodiments, the weight loss in an individual with type 2 diabetes is about 9 kg.

In some embodiments, the weight loss in an individual with baseline impaired fasting glucose is at least about 5 kg. In some embodiments, the weight loss in an individual with baseline impaired fasting glucose is at least about 10 kg. In some embodiments, the weight loss in an individual with baseline impaired fasting glucose is between about 10 and 15 kg. In some embodiments, the weight loss in an individual with baseline impaired fasting glucose is about 11 kg.

In some embodiments, the decrease in an assessment of weight comprises a decrease in hunger, a decrease in food cravings, or an increase in intermeal interval.

In some embodiments, the one or more additional beneficial effects comprise an improvement in one or more cardiovascular indications. In some embodiments, the improvement in one or more cardiovascular indications comprises one or more of a reduction in systolic and diastolic blood pressure (SBP and DBP, respectively), a decrease in heart rate, a decrease in total cholesterol, a decrease in LDL cholesterol, a decrease in HDL cholesterol, and/or a decrease in triglyceride levels.

In some embodiments, the one or more additional beneficial effects comprise a reduction in SBP.

In some embodiments, the reduction in SBP in an individual without type 2 diabetes is at least about 2 mmHg. In some embodiments, the reduction in SBP in an individual without type 2 diabetes is between 2 and 5 mmHg. In some embodiments, the reduction in SBP in an individual without type 2 diabetes is about 3 mmHg. In some embodiments, the reduction in SBP in an individual without type 2 diabetes is about 3.5 mmHg.

In some embodiments, the reduction in SBP in an individual with type 2 diabetes is at least about 2 mmHg. In some embodiments, the reduction in SBP in an individual with type 2 diabetes is between about 2 and 5 mmHg. In some embodiments, the reduction in SBP in an individual with type 2 diabetes is about 2.5 mmHg. In some embodiments, the reduction in SBP in an individual with type 2 diabetes is about 3 mmHg.

In some embodiments, the reduction in SBP in an individual with baseline impaired fasting glucose is at least about 1 mmHg. In some embodiments, the reduction in SBP in an individual with baseline impaired fasting glucose is between about 1 and 5 mmHg. In some embodiments, the reduction in SBP in an individual with baseline impaired fasting glucose is about 1.5 mmHg. In some embodiments, the reduction in SBP in an individual with baseline impaired fasting glucose is about 2 mmHg.

In some embodiments, the one or more additional beneficial effects comprise a reduction in DBP.

In some embodiments, the reduction in DBP in an individual without type 2 diabetes is at least about 1 mmHg. In some embodiments, the reduction in DBP in an individual without type 2 diabetes is at least between about 1 and 5 mmHg. In some embodiments, the reduction in DBP in an individual without type 2 diabetes is about 2 mmHg. In some embodiments, the reduction in DBP in an individual without type 2 diabetes is about 2.5 mmHg. In some embodiments, the reduction in DBP in an individual without type 2 diabetes is about 3 mmHg.

In some embodiments, the reduction in DBP in an individual with type 2 diabetes is at least about 1 mmHg. In some embodiments, the reduction in DBP in an individual with type 2 diabetes is between about 1 and 5 mmHg. In some embodiments, the reduction in DBP in an individual with type 2 diabetes is about 1.5 mmHg. In some embodiments, the reduction in DBP in an individual with type 2 diabetes is about 2 mmHg.

In some embodiments, the reduction in DBP in an individual with baseline impaired fasting glucose is at least about 1 mmHg. In some embodiments, the reduction in DBP in an individual with baseline impaired fasting glucose is between about 1 and 5 mmHg. In some embodiments, the reduction in DBP in an individual with baseline impaired fasting glucose is about 1.5 mmHg. In some embodiments, the reduction in DBP in an individual with baseline impaired fasting glucose is about 2 mmHg.

In some embodiments, the one or more additional beneficial effects comprise a reduction in heart rate.

In some embodiments, the reduction in heart rate in an individual without type 2 diabetes is at least about 2 BPM. In some embodiments, the reduction in heart rate in an individual without type 2 diabetes is between about 2 and 5 BPM. In some embodiments, the reduction in heart rate in an individual without type 2 diabetes is about 2 BPM. In some embodiments, the reduction in heart rate in an individual without type 2 diabetes is about 2.5 BPM. In some embodiments, the reduction in heart rate in an individual without type 2 diabetes is about 3 BPM.

In some embodiments, the reduction in heart rate in an individual with type 2 diabetes is at least about 2 BPM. In some embodiments, the reduction in heart rate in an individual with type 2 diabetes is between about 2 and 5 BPM. In some embodiments, the reduction in heart rate in an individual with type 2 diabetes is about 3 BPM. In some embodiments, the reduction in heart rate in an individual with type 2 diabetes is about 3.5 BPM.

In some embodiments, the reduction in heart rate in an individual with baseline impaired fasting glucose is at least about 2 BPM. In some embodiments, the reduction in heart rate in an individual with baseline impaired fasting glucose is between about 2 and 5 BPM. In some embodiments, the reduction in heart rate in an individual with baseline impaired fasting glucose is about 3.5 BPM. In some embodiments, the reduction in heart rate in an individual with baseline impaired fasting glucose is about 4 BPM.

In some embodiments, the improvement in glycemia comprises a decrease in total cholesterol level.

In some embodiments, the decrease in total cholesterol level in patients without type 2 diabetes is at least about 1 mg/dL. In some embodiments, the decrease in total cholesterol level in patients without type 2 diabetes is at least about 1.5 mg/dL. In some embodiments, the decrease in total cholesterol level in patients without type 2 diabetes is between about 1.5 and 2 mg/dL. In some embodiments, the decrease in total cholesterol level in patients without type 2 diabetes is about 1.7 mg/dL.

In some embodiments, the decrease in total cholesterol level in patients with type 2 diabetes is at least about 0.5 mg/dL. In some embodiments, the decrease in total cholesterol level in patients with type 2 diabetes is between about 0.5 and 1 mg/dL. In some embodiments, the decrease in total cholesterol level in patients with typo 2 diabetes is about 0.7 mg/dL.

In some embodiments, the decrease in total cholesterol level in patients with baseline impaired fasting glucose is at least about 2 mg/dL. In some embodiments, the decrease in total cholesterol level in patients with baseline impaired fasting glucose is between about 2 and 3 mg/dL. In some embodiments, the decrease in total cholesterol level in patients with baseline impaired fasting glucose is about 2.3 mg/dL.

In some embodiments, the improvement in glycemia comprises a decrease in LDL cholesterol level.

In some embodiments, the decrease in LDL cholesterol level in patients without type 2 diabetes is at least about 1 mg/dL. In some embodiments, the decrease in LDL cholesterol level in patients without type 2 diabetes is between about 1 and 2 mg/dL. In some embodiments, the decrease in LDL cholesterol level in patients without type 2 diabetes is about 1.1 mg/dL.

In some embodiments, the decrease in LDL cholesterol level in patients with type 2 diabetes is at least about 1 mg/dL. In some embodiments, the decrease in LDL cholesterol level in patients with type 2 diabetes is between about 1 and 1.5 mg/dL. In some embodiments, the decrease in LDL cholesterol level in patients with type 2 diabetes is about 1.4 mg/dL.

In some embodiments, the decrease in LDL cholesterol level in patients with baseline impaired fasting glucose is at least about 2 mg/dL. In some embodiments, the decrease in LDL cholesterol level in patients with baseline impaired fasting glucose is between about 2 and 3 mg/dL. In some embodiments, the decrease in LDL cholesterol level in patients with baseline impaired fasting glucose is about 2.5 mg/dL.

In some embodiments, the improvement in glycemia comprises a decrease in HDL cholesterol level.

In some embodiments, the decrease in HDL cholesterol level in patients without type 2 diabetes is at least about 4 mg/dL. In some embodiments, the decrease in HDL cholesterol level in patients without type 2 diabetes is between about 3 and 6 mg/dL. In some embodiments, the decrease in HDL cholesterol level in patients without type 2 diabetes is about 4.6 mg/dL.

In some embodiments, the decrease in HDL cholesterol level in patients with type 2 diabetes is at least about 5 mg/dL. In some embodiments, the decrease in HDL cholesterol level in patients with type 2 diabetes is at least about 7 mg/dL. In some embodiments, the decrease in HDL cholesterol level in patients with type 2 diabetes is between about 7 and 10 mg/dL. In some embodiments, the decrease in HDL cholesterol level in patients with type 2 diabetes is about 8.8 mg/dL.

In some embodiments, the decrease in HDL cholesterol level in patients with baseline impaired fasting glucose is at least about 2 mg/dL. In some embodiments, the decrease in HDL cholesterol level in patients with baseline impaired fasting glucose is between about 2 and 3 mg/dL. In some embodiments, the decrease in HDL cholesterol level in patients with baseline impaired fasting glucose is about 2.1 mg/dL.

In some embodiments, the one or more additional beneficial effects comprise an improvement in glycemia. In some embodiments, the improvement in glycemia comprises a reduction in fasting plasma glucose and/or a reduction in glycated hemoglobin (A1C) levels.

In some embodiments, the improvement in glycemia comprises a reduction in fasting plasma glucose.

In some embodiments, the reduction in fasting plasma glucose in patients without type 2 diabetes is at least about 1 mg/dL. In some embodiments, the reduction in fasting plasma glucose in patients without type 2 diabetes is at least about 1.5 mg/dL. In some embodiments, the reduction in fasting plasma glucose in patients without type 2 diabetes is between about 1 and 4 mg/dL. In some embodiments, the reduction in fasting plasma glucose in patients without type 2 diabetes is about 2.2 mg/dL.

In some embodiments, the reduction in fasting plasma glucose in patients with type 2 diabetes is at least about 10 mg/dL. In some embodiments, the reduction in fasting plasma glucose in patients with type 2 diabetes is between about 10 and 40 mg/dL. In some embodiments, the reduction in fasting plasma glucose in patients with type 2 diabetes is about 25 mg/dL. In some embodiments, the reduction in fasting plasma glucose in patients with type 2 diabetes is about 30 mg/dL.

In some embodiments, the reduction in fasting plasma glucose in patients with baseline impaired fasting glucose is at least about 5 mg/dL. In some embodiments, the reduction in fasting plasma glucose in patients with baseline impaired fasting glucose is between about 5 and 10 mg/dL. In some embodiments, the reduction in fasting plasma glucose in patients with baseline impaired fasting glucose is about 7 mg/dL. In some embodiments, the reduction in fasting plasma glucose in patients with baseline impaired fasting glucose is about 8 mg/dL.

In some embodiments, the improvement in glycemia comprises a reduction in glycated hemoglobin (A1C) levels.

In some embodiments, the reduction in glycated hemoglobin (A1C) level in patients without type 2 diabetes is at least about 0.1%. In some embodiments, the reduction in glycated hemoglobin (A1C) level in patients without type 2 diabetes is between about 0.1 and 0.2%. In some embodiments, the reduction in glycated hemoglobin (A1C) level in patients without type 2 diabetes is about 0.15%. In some embodiments, the reduction in glycated hemoglobin (A1C) level in patients without type 2 diabetes is about 0.18%.

In some embodiments, the reduction in glycated hemoglobin (A1C) level in patients with type 2 diabetes is at least about 0.5%. In some embodiments, the reduction in glycated hemoglobin (A1C) level in patients with type 2 diabetes is between about 1 and 2%. In some embodiments, the reduction in glycated hemoglobin (A1C) level in patients with type 2 diabetes is about 1.2%.

In some embodiments, the reduction in glycated hemoglobin (A1C) level in patients with baseline impaired fasting glucose is at least about 0.05%. In some embodiments, the reduction in glycated hemoglobin (A1C) level in patients with baseline impaired fasting glucose is between about 0.05 and 0.2%. In some embodiments, the reduction in glycated hemoglobin level (A1C) in patients with baseline impaired fasting glucose is about 0.1%.

In some embodiments, the improvement in glycemia comprises a decrease in triglyceride levels.

In some embodiments, the decrease in triglyceride level in patients without type 2 diabetes is at least about 5 mg/dL. In some embodiments, the decrease in triglyceride level in patients without type 2 diabetes is between about 5 and 20 mg/dL. In some embodiments, the decrease in triglyceride level in patients without type 2 diabetes is about 14 mg/dL. In some embodiments, the decrease in triglyceride level in patients without type 2 diabetes is about 14.5 mg/dL.

In some embodiments, the decrease in triglyceride level in patients with type 2 diabetes is at least about 10 mg/dL. In some embodiments, the decrease in triglyceride level in patients with type 2 diabetes is between about 10 and 20 mg/dL. In some embodiments, the decrease in triglyceride level in patients with type 2 diabetes is about 17 mg/dL. In some embodiments, the decrease in triglyceride level in patients with type 2 diabetes is about 17.8 mg/dL.

In some embodiments, the decrease in triglyceride level in patients with baseline impaired fasting glucose is at least about 5 mg/dL. In some embodiments, the decrease in triglyceride level in patients with baseline impaired fasting glucose is between about 5 and 20 mg/dL. In some embodiments, the decrease in triglyceride level in patients with baseline impaired fasting glucose is about 15 mg/dL.

Also provided is a method for weight management in an individual in need thereof, comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder according to any of the methods described herein or selected for treatment according to any of the methods described herein.

Also provided is a method for weight management in an individual in need thereof, comprising the steps of:
administering a therapeutically effective amount of (R)-8-chloro-1-methyl-2,3,4,5-tetrahydro-1H-3-benzazepine or a pharmaceutically acceptable salt, solvate or hydrate thereof to an individual,
wherein said individual has previously been determined to be a responder according to a method comprising the steps of:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual,
wherein if the individual has achieved a threshold effect after said first time period of administration, the individual is a responder.

Also provided is a method for weight management in an individual in need thereof, comprising the steps of:
administering a therapeutically effective amount of (R)-8-chloro-1-methyl-2,3,4,5-tetrahydro-1H-3-benzazepine or a pharmaceutically acceptable salt, solvate or hydrate thereof to an individual,
wherein said individual has previously been selected for treatment according to a method comprising the steps of:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual; and
selecting the individual for treatment with (R)-8-chloro-1-methyl-2,3,4,5-tetrahydro-1H-3-benzazepine or a pharmaceutically acceptable salt, solvate or hydrate thereof if the individual has achieved a threshold effect after said first time period of administration.

Also provided is a method for weight management in an individual in need thereof, comprising the steps of:
administering to the individual a therapeutically effective amount of (R)-8-chloro-1-methyl-2,3,4,5-tetrahydro-1H-3-benzazepine or a pharmaceutically acceptable salt, solvate or hydrate thereof;
determining whether the individual is a responder or is selected for treatment according to any of the methods described herein; and
continuing administration of the (R)-8-chloro-1-methyl-2,3,4,5-tetrahydro-1H-3-benzazepine or a pharmaceutically acceptable salt, solvate or hydrate thereof if the individual is identified as a responder, or
modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a method for weight management in an individual in need thereof, comprising the steps of:
administering to the individual a therapeutically effective amount of (R)-8-chloro-1-methyl-2,3,4,5-tetrahydro-1H-3-benzazepine or a pharmaceutically acceptable salt, solvate or hydrate thereof;
determining whether the individual is a responder according to a method comprising the steps of:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual,
wherein if the individual has achieved a threshold effect after said first time period of administration, the individual is a responder; and
continuing administration of the (R)-8-chloro-1-methyl-2,3,4,5-tetrahydro-1H-3-benzazepine or a pharmaceutically acceptable salt, solvate or hydrate thereof if the individual is identified as a responder, or
modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder.

Also provided is a method for assisting weight management in an individual in need thereof, comprising the steps of:
measuring whether wherein said individual is a responder according to any of the methods described herein or selected for treatment according to any of the methods described herein,
wherein a measurement that the individual is a responder or is selected for treatment indicates that the individual is suitable for prescription of a therapeutically effective amount of (R)-8-chloro-1-methyl-2,3,4,5-tetrahydro-1H-3-benzazepine or a pharmaceutically acceptable salt, solvate or hydrate thereof.

Also provided is a method for assisting weight management in an individual in need thereof, comprising the steps of:
measuring the individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual,
wherein a measurement that the individual has achieved a threshold effect after said first time period of administration indicates that the individual is a responder and is suitable for prescription of a a therapeutically effective amount of (R)-8-chloro-1-methyl-2,3,4,5-tetrahydro-1H-3-benzazepine or a pharmaceutically acceptable salt, solvate or hydrate thereof to an individual.

Also provided is a method for assisting weight management in an individual in need thereof, comprising the steps of:
measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual;
wherein a measurement that the individual has achieved a threshold effect after said first time period of administration of (R)-8-chloro-1-methyl-2,3,4,5-tetrahydro-1H-3-benzazepine or a pharmaceutically acceptable salt, solvate or hydrate thereof indicates that the individual is suitable for selection for prescription of a therapeutically effective amount of (R)-8-chloro-1-methyl-2,3,4,5-tetrahydro-1H-3-benzazepine or a pharmaceutically acceptable salt, solvate or hydrate thereof to an individual.

Also provided is a method for assisting weight management in an individual in need thereof, comprising the steps of:
measuring whether the individual is a responder or is selected for treatment according to any of the methods described herein,
wherein a measurement that the individual is a responder indicates that the individual is suitable for continuing prescription of a therapeutically effective amount of (R)-8- chloro-1-methyl-2,3,4,5-tetrahydro-1H-3-benzazepine or a pharmaceutically acceptable salt, solvate or hydrate thereof; and wherein a measurement that the individual is not a responder indicates that the individual is suitable for a modified prescription of the (R)-8-chloro-1-methyl-2,3,4,5-tetrahydro-1H-3-benzazepine or a pharmaceutically acceptable salt, solvate or hydrate.

Also provided is a method for assisting weight management in an individual in need thereof, comprising the steps of:

measuring whether the individual is a responder according to a method comprising the steps of:

measuring an individual's responsiveness to (R)-8-chloro-1-methyl-2,3,4,5-tetrahydro-1H-3-benzazepine or a pharmaceutically acceptable salt, solvate or hydrate thereof after a first time period of administration of (R)-8-chloro-1-methyl-2,3,4,5-tetrahydro-1H-3-benzazepine or a pharmaceutically acceptable salt, solvate or hydrate thereof to the individual, wherein if the individual has achieved a threshold effect after said first time period of administration, the individual is a responder; and wherein a measurement that the individual is a responder indicates that the individual is suitable for a continuing prescription of the (R)-8-chloro-1-methyl-2,3,4,5-tetrahydro-1H-3-benzazepine or a pharmaceutically acceptable salt, solvate or hydrate, or wherein a measurement that the individual is not a responder indicates that the individual is suitable for a modified prescription of the (R)-8-chloro-1-methyl-2,3,4,5-tetrahydro-1H-3-benzazepine or a pharmaceutically acceptable salt, solvate or hydrate thereof.

In some embodiments, modifying the administration of the (R)-8-chloro-1-methyl-2,3,4,5-tetrahydro-1H-3-benzazepine or a pharmaceutically acceptable salt, solvate or hydrate thereof comprises increasing the dose and/or frequency of administration of the (R)-8-chloro-1-methyl-2,3,4,5-tetrahydro-1H-3-benzazepine or a pharmaceutically acceptable salt, solvate or hydrate thereof.

In some embodiments, modifying the administration of the (R)-8-chloro-1-methyl-2,3,4,5-tetrahydro-1H-3-benzazepine or a pharmaceutically acceptable salt, solvate or hydrate thereof comprises prescribing or administering a weight loss compound or procedure to the individual to be used in combination with the (R)-8-chloro-1-methyl-2,3,4,5-tetrahydro-1H-3-benzazepine or a pharmaceutically acceptable salt, solvate or hydrate thereof.

Combinations of (R)-8-chloro-1-methyl-2,3,4,5-tetrahydro-1H-3-benzazepine with other agents, including without limitation, phentermine, and uses of such combinations in therapy are described in WO 2006/071740, which is incorporated herein by reference in its entirety. In some embodiments, the weight loss compound is selected from amphetamine, caffeine, bromocriptine, ephedrine, pseudoephedrine, phenylpropanolamine, diethylpropion, benzphetamine, rimonabant, mazindol, surinabant, orlistat, cetilistat, sibutramine, bupropion, citalopram, escitalopram, fluoxetine, paroxetine, sertraline, duloxetine, milnacipran, mirtazapine, venlafaxine, desvenlafaxine, topiramate, zonisamide, metformin, exenatide, pramlintide, liraglutide, obinepitide, naltrexone, phentermine, phendimetrazine, insulin, dexfenfluramine, fenfluramine, leptin, naltrexone, and pharmaceutically acceptable salts and combinations thereof. In some embodiments, the weight loss compound is phentermine.

In some embodiments, modifying the administration of the (R)-8-chloro-1-methyl-2,3,4,5-tetrahydro-1H-3-benzazepine or a pharmaceutically acceptable salt, solvate or hydrate thereof comprises prescribing or administering to the individual a weight loss compound chosen from cannabinoid CB1 receptor antagonists, lipase inhibitors, monoamine reuptake inhibitors, anticonvulsants, glucose sensitizers, incretin mimetics, amylin analogs, GLP-1 analogs, Y receptor peptides, 5HT2C serotonin receptor agonists, opioid receptor antagonists, appetite suppressants, anorectics, and hormones.

In some embodiments, modifying the administration of the (R)-8-chloro-1-methyl-2,3,4,5-tetrahydro-1H-3-benzazepine or a pharmaceutically acceptable salt, solvate or hydrate thereof comprises prescribing or administering to the individual a weight loss compound chosen from amphetamine, caffeine, bromocriptine, ephedrine, pseudoephedrine, phenylpropanolamine, diethylpropion, benzphetamine, rimonabant, mazindol, surinabant, orlistat, cetilistat, sibutramine, bupropion, citalopram, escitalopram, fluoxetine, paroxetine, sertraline, duloxetine, milnacipran, mirtazapine, venlafaxine, desvenlafaxine, topiramate, zonisamide, metformin, exenatide, pramlintide, liraglutide, obinepitide, naltrexone, phentermine, phendimetrazine, insulin, dexfenfluramine, fenfluramine, leptin, naltrexone, and pharmaceutically acceptable salts and combinations thereof.

In some embodiments, modifying the administration of the (R)-8-chloro-1-methyl-2,3,4,5-tetrahydro-1H-3-benzazepine or a pharmaceutically acceptable salt, solvate or hydrate thereof comprises discontinuing the prescribing or administering of the (R)-8-chloro-1-methyl-2,3,4,5-tetrahydro-1H-3-benzazepine or a pharmaceutically acceptable salt, solvate or hydrate thereof.

In some embodiments, the procedure comprises a surgical weight loss procedure.

In some embodiments, the methods for weight management further comprise prescribing and/or administering a reduced-calorie diet.

In some embodiments, the methods for weight management further comprise prescribing and/or administering a program of regular exercise.

In some embodiments, the methods for weight management further comprise prescribing and/or administering phentermine to the individual.

In some embodiments, weight management comprises weight loss.

In some embodiments, weight management comprises maintenance of weight loss.

In some embodiments, the terms "(R)-8-chloro-1-methyl-2,3,4,5-tetrahydro-1H-3-benzazepine or a pharmaceutically acceptable salt, solvate, or hydrate thereof" and "(R)-8-chloro-1-methyl-2,3,4,5-tetrahydro-1H-3-benzazepine, and pharmaceutically acceptable salts, solvates, and hydrates thereof" as used herein encompass any one of the following salts, or a Markush group comprising any combination of the following salts:

(R)-8-chloro-1-methyl-2,3,4,5-tetrahydro-1H-3-benzazepine hydrochloride salt;

(R)-8-chloro-1-methyl-2,3,4,5-tetrahydro-1H-3-benzazepine hydrobromide salt;

(R)-8-chloro-1-methyl-2,3,4,5-tetrahydro-1H-3-benzazepine hydroiodide salt;

(R)-8-chloro-1-methyl-2,3,4,5-tetrahydro-1H-3-benzazepine maleate salt;

(R)-8-chloro-1-methyl-2,3,4,5-tetrahydro-1H-3-benzazepine fumarate salt; and (R)-8-chloro-1-methyl-2,3,4,5-tetrahydro-1H-3-benzazepine hemifumarate salt;

(R)-8-chloro-1-methyl-2,3,4,5-tetrahydro-1H-3-benzazepine orotate salt;

(R)-8-chloro-1-methyl-2,3,4,5-tetrahydro-1H-3-benzazepine di-acetamidobenzoate salt-cocrystal;

(R)-8-chloro-1-methyl-2,3,4,5-tetrahydro-1H-3-benzazepine trans-cinnamate salt;

(R)-8-chloro-1-methyl-2,3,4,5-tetrahydro-1H-3-benzazepine heminapadisilate salt;

(R)-8-chloro-1-methyl-2,3,4,5-tetrahydro-1H-3-benzazepine (±)-mandelate salt;

(R)-8-chloro-1-methyl-2,3,4,5-tetrahydro-1H-3-benzazepine hemipamoate salt;

(R)-8-chloro-1-methyl-2,3,4,5-tetrahydro-1H-3-benzazepine (1S)-(+)-10-camsylate salt;

(R)-8-chloro-1-methyl-2,3,4,5-tetrahydro-1H-3-benzazepine hemi-L-malate salt;

(R)-8-chloro-1-methyl-2,3,4,5-tetrahydro-1H-3-benzazepine L-glutamate salt;

(R)-8-chloro-1-methyl-2,3,4,5-tetrahydro-1H-3-benzazepine L-aspartate salt;

(R)-8-chloro-1-methyl-2,3,4,5-tetrahydro-1H-3-benzazepine hemimucate salt;

(R)-8-chloro-1-methyl-2,3,4,5-tetrahydro-1H-3-benzazepine pyroglutamate salt;

(R)-8-chloro-1-methyl-2,3,4,5-tetrahydro-1H-3-benzazepine glucuronate salt;

(R)-8-chloro-1-methyl-2,3,4,5-tetrahydro-1H-3-benzazepine di-camphorate salt;

(R)-8-chloro-1-methyl-2,3,4,5-tetrahydro-1H-3-benzazepine bisulfate salt;

(R)-8-chloro-1-methyl-2,3,4,5-tetrahydro-1H-3-benzazepine hemisulfate salt;

(R)-8-chloro-1-methyl-2,3,4,5-tetrahydro-1H-3-benzazepine mesylate salt;

(R)-8-chloro-1-methyl-2,3,4,5-tetrahydro-1H-3-benzazepine hydrobromide salt;

(R)-8-chloro-1-methyl-2,3,4,5-tetrahydro-1H-3-benzazepine nitrate salt;

(R)-8-chloro-1-methyl-2,3,4,5-tetrahydro-1H-3-benzazepine sesqui-oxalate salt-cocrystal;

(R)-8-chloro-1-methyl-2,3,4,5-tetrahydro-1H-3-benzazepine adipate salt;

(R)-8-chloro-1-methyl-2,3,4,5-tetrahydro-1H-3-benzazepine malonate salt;

(R)-8-chloro-1-methyl-2,3,4,5-tetrahydro-1H-3-benzazepine hemimalonate salt;

(R)-8-chloro-1-methyl-2,3,4,5-tetrahydro-1H-3-benzazepine glycolate salt;

(R)-8-chloro-1-methyl-2,3,4,5-tetrahydro-1H-3-benzazepine hemi-edisylate salt;

(R)-8-chloro-1-methyl-2,3,4,5-tetrahydro-1H-3-benzazepine phosphate salt;

(R)-8-chloro-1-methyl-2,3,4,5-tetrahydro-1H-3-benzazepine citrate salt;

(R)-8-chloro-1-methyl-2,3,4,5-tetrahydro-1H-3-benzazepine hemi-oxalate salt;

(R)-8-chloro-1-methyl-2,3,4,5-tetrahydro-1H-3-benzazepine succinate salt; and (R)-8-chloro-1-methyl-2,3,4,5-tetrahydro-1H-3-benzazepine oxoglutarate salt; and pharmaceutically acceptable solvates and hydrates thereof.

In some embodiments, the terms "(R)-8-chloro-1-methyl-2,3,4,5-tetrahydro-1H-3-benzazepine or a pharmaceutically acceptable salt, solvate, or hydrate thereof" and "(R)-8-chloro-1-methyl-2,3,4,5-tetrahydro-1H-3-benzazepine, and pharmaceutically acceptable salts, solvates, and hydrates thereof" as used herein encompass any one of the following salts, or a Markush group comprising any combination of the following salts:

(R)-8-chloro-1-methyl-2,3,4,5-tetrahydro-1H-3-benzazepine hydrochloride salt;

(R)-8-chloro-1-methyl-2,3,4,5-tetrahydro-1H-3-benzazepine hydrochloride salt hemihydrate;

(R)-8-chloro-1-methyl-2,3,4,5-tetrahydro-1H-3-benzazepine hydrochloride salt hydrate;

(R)-8-chloro-1-methyl-2,3,4,5-tetrahydro-1H-3-benzazepine hydrobromide salt;

(R)-8-chloro-1-methyl-2,3,4,5-tetrahydro-1H-3-benzazepine hydroiodide salt;

(R)-8-chloro-1-methyl-2,3,4,5-tetrahydro-1H-3-benzazepine maleate salt;

(R)-8-chloro-1-methyl-2,3,4,5-tetrahydro-1H-3-benzazepine fumarate salt;

(R)-8-chloro-1-methyl-2,3,4,5-tetrahydro-1H-3-benzazepine hemifumarate salt;

(R)-8-chloro-1-methyl-2,3,4,5-tetrahydro-1H-3-benzazepine orotate salt;

(R)-8-chloro-1-methyl-2,3,4,5-tetrahydro-1H-3-benzazepine orotate salt hydrate;

(R)-8-chloro-1-methyl-2,3,4,5-tetrahydro-1H-3-benzazepine di-4-acetamidobenzoate salt-cocrystal methyl ethyl ketone solvate;

(R)-8-chloro-1-methyl-2,3,4,5-tetrahydro-1H-3-benzazepine trans-cinnamate salt;

(R)-8-chloro-1-methyl-2,3,4,5-tetrahydro-1H-3-benzazepine heminapadisilate salt;

(R)-8-chloro-1-methyl-2,3,4,5-tetrahydro-1H-3-benzazepine heminapadisilate salt solvate 1;

(R)-8-chloro-1-methyl-2,3,4,5-tetrahydro-1H-3-benzazepine heminapadisilate salt solvate 2;

(R)-8-chloro-1-methyl-2,3,4,5-tetrahydro-1H-3-benzazepine (±)-mandelate salt hydrate;

(R)-8-chloro-1-methyl-2,3,4,5-tetrahydro-1H-3-benzazepine hemipamoate salt hydrate;

(R)-8-chloro-1-methyl-2,3,4,5-tetrahydro-1H-3-benzazepine (1S)-(+)-10-camsylate salt;

(R)-8-chloro-1-methyl-2,3,4,5-tetrahydro-1H-3-benzazepine hemi-L-malate salt;

(R)-8-chloro-1-methyl-2,3,4,5-tetrahydro-1H-3-benzazepine L-glutamate salt;

(R)-8-chloro-1-methyl-2,3,4,5-tetrahydro-1H-3-benzazepine L-aspartate salt;

(R)-8-chloro-1-methyl-2,3,4,5-tetrahydro-1H-3-benzazepine hemimucate salt;

(R)-8-chloro-1-methyl-2,3,4,5-tetrahydro-1H-3-benzazepine pyroglutamate salt;

(R)-8-chloro-1-methyl-2,3,4,5-tetrahydro-1H-3-benzazepine glucuronate salt;

(R)-8-chloro-1-methyl-2,3,4,5-tetrahydro-1H-3-benzazepine di-camphorate salt solvate;

(R)-8-chloro-1-methyl-2,3,4,5-tetrahydro-1H-3-benzazepine bisulfate salt;

(R)-8-chloro-1-methyl-2,3,4,5-tetrahydro-1H-3-benzazepine hemisulfate salt hydrate;

(R)-8-chloro-1-methyl-2,3,4,5-tetrahydro-1H-3-benzazepine mesylate salt;

(R)-8-chloro-1-methyl-2,3,4,5-tetrahydro-1H-3-benzazepine hydrobromide salt hemihydrate;

(R)-8-chloro-1-methyl-2,3,4,5-tetrahydro-1H-3-benzazepine nitrate salt;

(R)-8-chloro-1-methyl-2,3,4,5-tetrahydro-1H-3-benzazepine sesqui-oxalate salt-cocrystal;

(R)-8-chloro-1-methyl-2,3,4,5-tetrahydro-1H-3-benzazepine adipate salt;

(R)-8-chloro-1-methyl-2,3,4,5-tetrahydro-1H-3-benzazepine malonate salt;

(R)-8-chloro-1-methyl-2,3,4,5-tetrahydro-1H-3-benzazepine hemimalonate salt;

(R)-8-chloro-1-methyl-2,3,4,5-tetrahydro-1H-3-benzazepine glycolate salt;

(R)-8-chloro-1-methyl-2,3,4,5-tetrahydro-1H-3-benzazepine hemi-edisylate salt;

(R)-8-chloro-1-methyl-2,3,4,5-tetrahydro-1H-3-benzazepine phosphate salt;

(R)-8-chloro-1-methyl-2,3,4,5-tetrahydro-1H-3-benzazepine citrate salt hemihydrate;

(R)-8-chloro-1-methyl-2,3,4,5-tetrahydro-1H-3-benzazepine hemi-oxalate salt;

(R)-8-chloro-1-methyl-2,3,4,5-tetrahydro-1H-3-benzazepine succinate salt;

(R)-8-chloro-1-methyl-2,3,4,5-tetrahydro-1H-3-benzazepine oxoglutarate salt; and (R)-8-chloro-1-methyl-2,3,4,5-tetrahydro-1H-3-benzazepine oxoglutarate salt solvate.

In some embodiments, the (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride or a solvate or hydrate thereof.

In some embodiments, the (R)-8-chloro-1-methyl-2,3,4,5-tetrahydro-1H-3-benzazepine or a pharmaceutically acceptable salt, solvate or hydrate thereof is (R)-8-chloro-1-methyl-2,3,4,5-tetrahydro-1H-3-benzazepine hydrochloride hemihydrate.

It is understood that when the phrase "pharmaceutically acceptable salts, solvates and hydrates" or the phrase "pharmaceutically acceptable salt, solvate or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to compounds described herein that are salts, it embraces pharmaceutically acceptable solvates and/or hydrates of such salts.

It will be apparent to those skilled in the art that the dosage forms described herein may comprise, as the active component, either a compound described herein or a pharmaceutically acceptable salt or as a solvate or hydrate thereof. Moreover, various hydrates and solvates of the compounds described herein and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999. Accordingly, one aspect of the present disclosure pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

The present disclosure includes all isotopes of atoms occurring in the present salts and crystalline forms thereof. Isotopes include those atoms having the same atomic number but different mass numbers. One aspect of the present invention includes every combination of one or more atoms in the present salts and crystalline forms thereof that is replaced with an atom having the same atomic number but a different mass number. One such example is the replacement of an atom that is the most naturally abundant isotope, such as $^1$H or $^{12}$C, found in one the present salts and crystalline forms thereof, with a different atom that is not the most naturally abundant isotope, such as $^2$H or $^3$H (replacing $^1$H), or $^{11}$C, $^{13}$C, or $^{14}$C (replacing $^{12}$C). A salt wherein such a replacement has taken place is commonly referred to as being isotopically-labeled. Isotopic-labeling of the present salts and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C and $^{14}$C. Isotopes of nitrogen include $^{13}$N and $^{15}$N. Isotopes of oxygen include $^{15}$O, $^{17}$O, and $^{18}$C. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present salts and crystalline forms thereof, wherein the naturally occurring distribution of the isotopes in the composition is perturbed. Another aspect of the present invention includes compositions and pharmaceutical compositions comprising salts and crystalline forms thereof as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Also provided is a compound for use in a method for decreasing food intake in an individual in need thereof, said method comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any of the methods described herein; and wherein said compound is (R)-8-chloro-1-methyl-2,3,4,5-tetrahydro-1H-3-benzazepine or a pharmaceutically acceptable salt, solvate or hydrate thereof.

Also provided is a compound for use in a method for decreasing food intake in an individual in need thereof, said method comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to any of the methods described herein and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder;

wherein said compound is (R)-8-chloro-1-methyl-2,3,4,5-tetrahydro-1H-3-benzazepine or a pharmaceutically acceptable salt, solvate or hydrate thereof.

Also provided is a compound for use in a method for inducing satiety in an individual in need thereof, said method comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any of the methods described herein; and wherein said compound is (R)-8-chloro-1-methyl-2,3,4,5-tetrahydro-1,1-3-benzazepine or a pharmaceutically acceptable salt, solvate or hydrate thereof.

Also provided is a compound for use in a method for inducing satiety in an individual in need thereof, said method comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to any of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder;

wherein said compound is (R)-8-chloro-1-methyl-2,3,4,5-tetrahydro-1H-3-benzazepine or a pharmaceutically acceptable salt, solvate or hydrate thereof.

Also provided is a compound for use in a method for the treatment of obesity in an individual in need thereof, said method comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to be a responder or selected for treatment according to any of the methods described herein; and wherein said compound is (R)-8-chloro-1-methyl-2,3,4,5-tetrahydro-1H-3-benzazepine or a pharmaceutically acceptable salt, solvate or hydrate thereof.

Also provided is a compound for use in a method for the treatment of obesity in an individual in need thereof, said method comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to any of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder;

wherein said compound is (R)-8-chloro-1-methyl-2,3,4,5-tetrahydro-1H-3-benzazepine or a pharmaceutically acceptable salt, solvate or hydrate thereof.

Also provided is a compound for use in a method for the prevention of obesity in an individual in need thereof, said method comprising the steps of:

administering a therapeutically effective amount of (R)-8-chloro-1-methyl-2,3,4,5-tetrahydro-1H-3-benzazepine or a pharmaceutically acceptable salt, solvate or hydrate thereof to an individual, wherein said individual has previously been determined to a responder or selected for treatment according to any of the methods described herein; and wherein said compound is (R)-8-chloro-1-methyl-2,3,4,5-tetrahydro-1,1-3-benzazepine or a pharmaceutically acceptable salt, solvate or hydrate thereof.

Also provided is a compound for use in a method for the prevention of obesity in an individual in need thereof, said method comprising the steps of:

administering to the individual a therapeutically effective amount of (R)-8-chloro-1-methyl-2,3,4,5-tetrahydro-1H-3-benzazepine or a pharmaceutically acceptable salt, solvate or hydrate thereof;

determining whether the individual is a responder or is selected for treatment according to any of the methods described herein; and continuing administration of the (R)-8-chloro-1-methyl-2,3,4,5-tetrahydro-1H-3-benzazepine or a pharmaceutically acceptable salt, solvate or hydrate thereof if the individual is identified as a responder, or modifying the administration of the (R)-8-chloro-1-methyl-2,3,4,5-tetrahydro-1H-3-benzazepine or a pharmaceutically acceptable salt, solvate or hydrate thereof to the individual if the individual is not identified as a responder;

wherein said compound is (R)-8-chloro-1-methyl-2,3,4,5-tetrahydro-1H-3-benzazepine or a pharmaceutically acceptable salt, solvate or hydrate thereof.

Also provided is a composition for use in a method of weight management in an individual, comprising:

a therapeutically effective amount of (R)-8-chloro-1-methyl-2,3,4,5-tetrahydro-1H-3-benzazepine or a pharmaceutically acceptable salt, solvate or hydrate thereof;

wherein the individual has previously been determined to be a responder according to any of the methods described herein or selected for treatment according to any of the methods described herein.

Also provided is a kit for use in a method of weight management in an individual, comprising:

a therapeutically effective amount of (R)-8-chloro-1-methyl-2,3,4,5-tetrahydro-1H-3-benzazepine or a pharmaceutically acceptable salt, solvate or hydrate thereof; and instructions indicating that the (R)-8-chloro-1-methyl-2,3,4,5-tetrahydro-1H-3-benzazepine or a pharmaceutically acceptable salt, solvate or hydrate thereof is to be administered to an individual who has previously been determined to be a responder according to any of the methods described herein or selected for treatment according to any of the methods described herein.

In some embodiments, the kit further comprises phentermine.

In some embodiments, the (R)-8-chloro-1-methyl-2,3,4,5-tetrahydro-1H-3-benzazepine hydrochloride or a solvate or hydrate thereof is prescribed and/or administered to the individual in a dose equal to or less than 20 mg per day.

In some embodiments, the (R)-8-chloro-1-methyl-2,3,4,5-tetrahydro-1H-3-benzazepine hydrochloride or a solvate or hydrate thereof is prescribed and/or administered to the individual in a dose equal to or less than 10 mg twice per day.

In some embodiments, the (R)-8-chloro-1-methyl-2,3,4,5-tetrahydro-1H-3-benzazepine or a pharmaceutically acceptable salt, solvate or hydrate thereof is administered in a tablet suitable for oral administration.

Conventional excipients, such as binding agents, fillers, acceptable wetting agents, tabletting lubricants and disintegrants can be used in tablets and capsules for oral administration. Liquid preparations for oral administration can be in the form of solutions, emulsions, aqueous or oily suspensions and syrups. Alternatively, the oral preparations can be in the form of dry powder that can be reconstituted with water or another suitable liquid vehicle before use. Additional additives such as suspending or emulsifying agents, non-aqueous vehicles (including edible oils), preservatives and flavorings and colorants can be added to the liquid preparations. Parenteral dosage forms can be prepared by dissolving the compound in a suitable liquid vehicle and filter sterilizing the solution before filling and sealing an appropriate vial or ampule. These are just a few examples of the many appropriate methods well known in the art for preparing dosage forms. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a compound can, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, together with a conventional adjuvant, carrier, or diluent, can thus be placed into the form of pharmaceutical formulations and unit dosages thereof and in such form may be employed as solids, such as tablets or filled capsules, or liquids, such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof can comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition can be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

The dose when using the compounds provided herein can vary within wide limits and as is customary and is known to the physician, it is to be tailored to the individual conditions in each individual case. It depends, for example, on the nature and severity of the illness to be treated, on the condition of the patient, on the compound employed, on whether an acute or chronic disease state is treated or prophylaxis conducted or on whether further active compounds are administered in addition to the compounds provided herein. Representative doses include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the healthcare provider it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis conducted or whether further active compounds are administered in addition to the compounds provided herein such as part of a drug combination. The dosage regimen for treating a disease condition with the compounds and/or compositions provided herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods disclosed herein.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds provided herein can be administrated in a wide variety of oral and parenteral dosage forms. It will be obvious to those skilled in the art that the dosage forms may comprise, as the active component, either a compound provided herein or a pharmaceutically acceptable salt, solvate or hydrate of a compound provided herein.

Some embodiments include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

EXAMPLES

Example 1

Phase 3 Studies

APD356-009 ("BLOOM") was a 104-week, placebo controlled study that assessed the safety and efficacy of lorcaserin 10 mg BID in overweight and obese patients, with concurrent behavior modification. The primary efficacy objective during Year 1 was to evaluate weight loss; the primary objective during Year 2 was to assess the ability of lorcaserin to maintain body weight loss that was achieved during Year 1. At study start, each patient received randomized, double blind treatment assignments for Year 1 and for Year 2 (all patients were given a new randomization number for Year 2 to assure that patients and study personnel remained blinded to treatment assignments). All patients assigned to placebo during Year 1 (50% of randomized population) remained on placebo in Year 2. Patients assigned to lorcaserin during Year 1 were randomly assigned to stay on lorcaserin during Year 2 (⅔ of Year 1 lorcaserin patients) or to switch to placebo (⅓ of Year 1 lorcaserin patients). Lorcaserin met the pre-specified Year 1 categorical and mean weight loss endpoints, and the Year 2 weight maintenance endpoint.

APD356-010 (BLOOM-DM) was a 52-week, placebo controlled study that evaluated the effect of two lorcaserin doses (10 mg BID and 10 mg QD) on categorical and total weight loss with concurrent behavior modification in 604 patients with type 2 diabetes mellitus managed with oral hypoglycemic agents. Randomization to the 10 mg once daily group was halted by protocol amendment in order to accelerate enrollment, resulting in final group sizes of 253 (placebo), 95 (lorcaserin QD) and 256 (lorcaserin BID). Lorcaserin at both doses met the three pre-defined co-primary efficacy endpoints for efficacy. Greater proportions of patients treated with lorcaserin achieved 5% and 10% categorical weight loss as compared to patients treated with placebo, and patients on lorcaserin achieved a significantly greater mean weight loss.

APD356-011 ("BLOSSOM") was a 52-week, placebo controlled study that evaluated the effect of two lorcaserin doses (10 mg BID and 10 mg QD) on categorical and total weight loss with concurrent behavior modification. Patients were randomized in a ratio of 2:1:2 to lorcaserin 10 mg BID, 10 mg QD, or placebo. Lorcaserin 10 mg QD and BID met the pre-defined co-primary efficacy endpoints.

Example 2

Identifying Responders Based on Early Weight Loss

An analysis of early weight loss was performed, at each visit after baseline through Week 24, as a predictor of ultimate weight loss success, as defined by achieving at least about 5% weight loss at 52 weeks, or at least about 10% weight loss at 52 weeks. The area under the curve (AUC) for the receiver operating characteristic (ROC) curve measures the balance between specificity and sensitivity by measuring how often a predictor (e.g., Week 12 or Week 24 percent weight loss) and a successful outcome (e.g., at least 5% or 10% weight loss at Week 52) are concordant.

At Week 12, the optimal thresholds were 4.6% and 5.9% weight loss for predicting at least 5% and at least 10% weight loss at Week 52. At Week 24, the optimal weight loss thresholds were 6.1% and 8.5%, respectively (Table 1 and Table 2). Non-diabetic patients who achieved at least 5% weight loss at Week 12, lost on average approximately 10.6 kilos (23 pounds) at Week 52, and approximately 86% and 50% of these patients respectively achieved at least 5% and 10% weight loss at Week 52. The positive and negative predictive values for this criterion were 85.5% and 74.0% for 5% weight loss at Week 52, and 49.8% and 95.3% for 10% weight loss at Week 52 (Table 3).

TABLE 1

AUCs for the ROC curves using percent weight change from baseline at each early visit (Weeks 2-24) as predictors for at least 5% weight loss at Week 52 (lorcaserin 10 mg BID)

| Percent Change from Baseline at: | % Weight Loss | AUC* | SE | 95% Confidence Interval |
|---|---|---|---|---|
| Week 2 | 1.5% | 0.687 | 0.015 | (0.658, 0.716) |
| Week 4 | 2.5% | 0.753 | 0.014 | (0.726, 0.780) |
| Week 8 | 3.9% | 0.802 | 0.012 | (0.778, 0.826) |
| Week 12 | 4.6% | 0.849 | 0.011 | (0.828, 0.870) |
| Week 24 | 6.1% | 0.912 | 0.008 | (0.897, 0.927) |

*Higher number signifies better prediction.

TABLE 2

AUCs for the ROC curves using percent weight change from baseline at each early visit (Weeks 2-24) as predictors for at least 10% weight loss at Week 52 (lorcaserin 10 mg BID)

Predictors:

| Percent Change from Baseline at | % Weight Loss | AUC* | SE | 95% Confidence Interval |
|---|---|---|---|---|
| Week 2 | 1.8 | 0.707 | 0.014 | (0.680, 0.735) |
| Week 4 | 3.2 | 0.777 | 0.014 | (0.752, 0.802) |
| Week 8 | 4.7 | 0.829 | 0.011 | (0.807, 0.851) |
| Week 12 | 5.9 | 0.866 | 0.010 | (0.845, 0.885) |
| Week 24 | 8.5 | 0.929 | 0.007 | (0.915, 0.942) |

*Higher number signifies better prediction.

Table 3 and Table 4 provide the sensitivity, specificity, positive predicted value (PPV) and negative predictive value (NPV) at Weeks 12 and 24 for at least about 5% and at least about 10% weight loss at Week 52 in different studies. The rounded percent weight loss at Week 12 for at least 5% and at least about 10% weight loss at Week 52 are about 5% and about 6%, respectively. Using the about 6% weight loss at Week 12 as a criterion enhances the PPV for both about 5% and about 10% categorical weight loss at Week 52, but at the expense of excluding about 10% and about 4% more of the about 5% categorical responders at Week 52 in patients without and with diabetes, respectively, based upon NPV. The rounded optimal thresholds at Week 24 for at least about 5% and at least about 10% weight loss at Week 52 are about 6% and about 9%, respectively. Using the 9% weight loss criterion at Week 24 enhances the PPV for both about 5% and about 10% categorical weight loss at Week 52, but at the expense of excluding about 19% and about 9% more of the about 5% categorical responders at Week 52 in patients without and with diabetes, respectively, based upon NPV. As described below, if at least about a 5% weight loss criterion is applied, patients achieving this milestone will achieve an average of about 10.8% weight loss in patients without diabetes and about 9.1% weight loss in patients with diabetes at Week 52.

TABLE 3

Sensitivity and Specificity Analyses for lorcaserin 10 mg BID use Week 12/Week 24 responder status as a predictor for Week 52 (Pooled BLOOM and BLOSSOM Studies)

| Criteria | Sensitivity | Specificity | PPV | NPV |
|---|---|---|---|---|
| Week 12: 5% and Week 52: 5% | 76.2% | 84.0% | 85.5% | 74.0% |
| Week 12: 5% and Week 52: 10% | 91.2% | 66.1% | 49.8% | 95.3% |
| Week 12: 6% and Week 52: 5% | 61.3 | 90.9 | 89.3 | 65.4 |
| Week 12: 6% and Week 52: 10% | 82.4 | 78.4 | 58.4 | 92.4 |
| Week 24: 6% and Week 52: 5% | 83.4 | 84.9 | 89.0 | 77.7 |
| Week 24: 6% and Week 52: 10% | 96.5 | 62.1 | 52.5 | 97.6 |
| Week 24: 9% and Week 52: 5% | 52.8 | 97.2 | 96.5 | 58.5 |
| Week 24: 9% and Week 52: 10% | 82.7 | 89.2 | 76.9 | 92.2 |

Note:
Only patients with observed Week 12 (Week 24) data are included in the above analyses.

TABLE 4

Sensitivity and Specificity Analyses for lorcaserin 10 mg BID use Week 12/Week 24 responder status as a predictor for Week 52 (BLOOM-DM Study)

| Criteria | Sensitivity | Specificity | PPV | NPV |
|---|---|---|---|---|
| Week 12: 5% and Week 52: 5% | 61.1% | 81.9% | 70.5% | 74.8% |
| Week 12: 5% and Week 52: 10% | 70.0% | 71.8% | 35.9% | 91.4% |
| Week 12: 6% and Week 52: 5% | 46.7 | 91.3 | 79.2 | 70.7 |
| Week 12: 6% and Week 52: 10% | 60.0 | 83.6 | 45.3 | 90.2 |
| Week 24: 6% and Week 52: 5% | 65.9 | 83.3 | 76.3 | 75.0 |
| Week 24: 6% and Week 52: 10% | 86.8 | 72.8 | 43.4 | 95.8 |
| Week 24: 9% and Week 52: 5% | 37.5 | 99.1 | 97.1 | 66.0 |
| Week 24: 9% and Week 52: 10% | 65.8 | 94.3 | 73.5 | 92.0 |

Note:
Only patients with observed Week 12 (Week 24) data are included in the above analyses The proportion of non-diabetic patients who achieved at least 5% total body weight loss at Week 52 was greater for Week 12 responders than for Week 12 non-responders (see Table 5 and FIG. 1).

TABLE 5

| Week 12 | Completed Week 12$^a$ | Week 52 (MITT with LOCF) |
|---|---|---|
| ≥5% wt loss | 1,251/2,537 (49.3%) | 1,070/1,251 (85.5%) |
| <5% wt loss | 1,286/2,537 (50.7%) | 335/1,286 (26.0%) |

$^a$Percentage calculated based on number of patients with observed Week 12 data Example 3

Week 52 Outcomes for Those Achieving at least 5% Weight Loss at Week 12

In patients without type 2 diabetes mellitus (T2DM), proportions achieving ≥5% weight loss and weight loss at Week 52 for (R)-8-chloro-1-methyl-2,3,4,5-tetrahydro-1H-3-benzazepine hydrochloride salt hemihydrate ("drug") and placebo patients were 47 vs. 23% and 5.8 vs. 2.5 kg, respectively (MITT-LOCF). Results in patients with T2DM were 38 vs. 16% and 4.7 vs. 1.9 kg, respectively. Proportions meeting the ≥5% weight loss at Week 12 criterion were 49.3% and 35.9% for drug patients without and with T2DM, respectively, and 22.6% and 11.5% for placebo patients. Week 52 weight loss in non-diabetic drug Week 12 responders was 10.6 kg (23 lbs), and 86% and 50% of patients achieved at least 5% and 10% weight loss. In diabetic drug Week 12 responders, results were 9.3 kg (20 lbs), 71%, and 36%.

Week 52 reductions in FPG and A1C in diabetic drug Week 12 responders were 29.3 mg/dL and 1.2%, and were 7.8 mg/dL and 0.4% in drug Week 12 responders with impaired fasting glucose (IFG) at baseline. Week 52 reductions in systolic and diastolic BP and heart rate were 3.4 mmHg, 2.5 mmHg, and 2.5 BPM in non-diabetic drug Week 12 responders, and 2.6 mmHg, 1.9 mmHg, and 3.2 BPM in drug Week 12 responders with T2DM.

Accordingly, achievement of ≥5% weight loss by Week 12 is a strong predictor of robust one-year responses in weight, cardiovascular vital signs, and glycemia. In one embodiment, based upon the predictive value for ≥5% weight loss at Week 52, drug should not be administered to an individual not losing at least about 5% at Week 12 (i.e., are not Week 12 responders).

Tables 6 and 7, below, present weight loss, vital sign, and glycemic changes at Week 52 in pooled patients without diabetes, patients with T2DM, and pooled patients with impaired fasting glucose (IFG; ≥100 mg/dL) who were Week 12 responders.

TABLE 6

Drug 10 mg BID patients

| | Patients without T2DM | | | Patients with T2DM | | | Patients with IFG | | |
|---|---|---|---|---|---|---|---|---|---|
| | N | BL | W52 Change | N | BL | W52 Change | N | BL | W52 Change |
| Weight Loss | 1251 | | | 78 | | | 170 | | |
| ≥5% (%) | | | 85.5 | | | 70.5 | | | 88.8 |
| ≥10% (%) | | | 49.8 | | | 35.9 | | | 52.4 |
| kg | | 99.0 | −10.6 | | 102.3 | −9.3 | | 104.3 | −11.2 |
| FPG (mg/dL) | | 94.7 | −2.2 | | 156.4 | −29.3 | | 107.2 | −7.8 |
| A1C (%) | | 5.6 | −0.18 | | 7.9 | −1.2 | | 5.8 | −0.11 |
| SBP (mmHg) | | 122.0 | −3.4 | | 129.0 | −2.6 | | 124.2 | −1.7 |
| DBP (mmHg) | | 77.6 | −2.5 | | 80.1 | −1.9 | | 78.6 | −1.5 |
| Heart Rate (bpm) | | 69.0 | −2.5 | | 73.3 | −3.2 | | 70.8 | −3.7 |
| Total Cholesterol (mg/dL)* | | 196.3 | −1.7 | | 168.4 | −0.7 | | 199.2 | −2.3 |
| LDL-C (mg/dL)* | | 115.4 | 1.1 | | 91.9 | 1.4 | | 116.5 | 2.5 |
| Triglycerides (mg/dL)* | | 139.7 | −14.5 | | 163.9 | −17.8 | | 150.7 | −15.5 |
| HDL-C (mg/dL)* | | 53.4 | 4.6 | | 46.0 | 8.8 | | 52.8 | 2.1 |

*For lipid parameters used percent change from baseine at Week 52

TABLE 7

Placebo Patients:

| | Patients without T2DM | | | Patients with T2DM | | | Patients with IFG | | |
|---|---|---|---|---|---|---|---|---|---|
| | N | BL | W52 Change | N | BL | W52 Change | N | BL | W52 Change |
| Weight Loss | 541 | | | 25 | | | 61 | | |
| ≥5% (%) | | | 76.2 | | | 60.0 | | | 78.7 |
| ≥10% (%) | | | 38.6 | | | 28.0 | | | 50.8 |
| kg | | 100.3 | −9.5 | | 103.1 | −7.5 | | 102.2 | −10.5 |
| FPG (mg/dL) | | 95.1 | −1.2 | | 157.2 | −24.2 | | 108.8 | −7.5 |
| A1C (%) | | 5.6 | −0.15 | | 8.1 | −1.1 | | 5.8 | −0.07 |
| SBP (mmHg) | | 123.7 | −3.6 | | 129.5 | −4.2 | | 127.4 | −4.6 |
| DBP (mmHg) | | 78.0 | −2.4 | | 80.8 | −2.6 | | 79.3 | −2.5 |
| Heart Rate (bpm) | | 69.1 | −2.5 | | 70.6 | 0.0 | | 70.4 | −5.7 |
| Total Cholesterol (mg/dL)* | | 197.5 | −0.5 | | 167.5 | 0.0 | | 208.3 | −1.7 |
| LDL-C (mg/dL)* | | 115.4 | 1.7 | | 90.1 | 5.6 | | 122.5 | 1.1 |
| Triglycerides (mg/dL)* | | 143.4 | −10.5 | | 160.7 | −15.6 | | 170.0 | −14.5 |
| HDL-C (mg/dL)* | | 53.4 | 5.7 | | 45.2 | 11.7 | | 52.4 | 4.5 |

*For lipid parameters used percent change from baseline at Week 52

Proportions of patients without diabetes with a Week 12 observation who had at least 5% weight loss at Week 12 (Week 12 responders), lorcaserin vs. placebo, were 49.3% vs. 22.6% (Table 8). Week 52 weight loss in lorcaserin Week 12 responders without diabetes was 10.6 kg (23 lbs), with 86% and 50% achieving at least 5% and 10% weight loss, respectively (Table 9 and FIG. 1). Proportions of Week 12 responders with type 2 diabetes, lorcaserin vs. placebo, were 35.9% vs. 11.5%. Week 52 weight loss in lorcaserin Week 12 responders with type 2 diabetes was 9.3 kg (20 lbs), with 71% and 36% achieving 5% and 10% weight loss, respectively.

Figure 2:
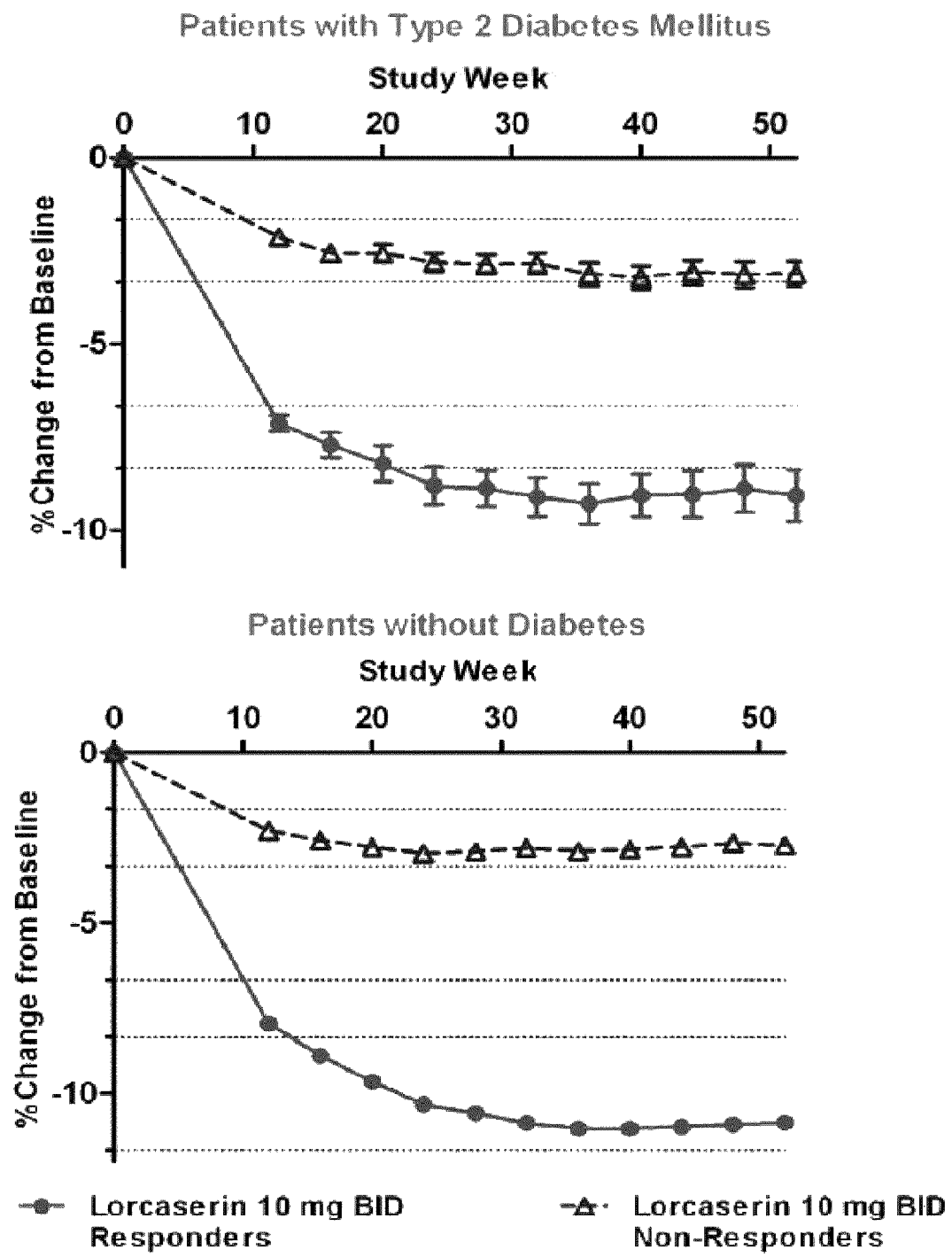
FIG. 2 shows the Week 52 weight loss in lorcaserin Week 12 responders with type 2 diabetes was 9.3 kg (20 lbs), with 71% and 36% achieving 5% and 10% weight loss, respectively.

FIG. 2 shows weight loss through Week 52 for Week 12 responders and non-responders with and without diabetes in both treatment groups. In patients with type 2 diabetes, change in HbA1c at Week 52 was −1.2% for lorcaserin Week 12 responders vs. −0.84% in non-responders (see Table 4). Week 52 reductions in systolic and diastolic blood pressure and heart rate were 3.4 mmHg, 2.5 mmHg, and 2.5 bpm in lorcaserin responders without diabetes, and 2.6 mmHg, 1.9 mmHg, and 3.2 bpm in lorcaserin responders with type 2 diabetes (Table 10).

TABLE 8

Number (%) of Patients with Observed Week 12 Data

|  | N Randomized | N with observed Week 12 data[a] | Week 12 Responder[b] | Week 12 Non-Responder[b] |
|---|---|---|---|---|
| Pooled BLOOM and BLOSSOM Studies |  |  |  |  |
| Lorcaserin 10 mg BID | 3198 | 2537 (79.3%) | 1251 (49.3%) | 1286 (50.7%) |
| Placebo | 3190 | 2393 (75.0%) | 541 (22.6%) | 1852 (77.4%) |
| BLOOM-DM Study |  |  |  |  |
| Lorcaserin 10 mg BID | 256 | 217 (84.8%) | 78 (35.9%) | 139 (64.1%) |
| Placebo | 253 | 217 (85.8%) | 25 (11.5%) | 192 (88.5%) |

[a]Percentage calculated based on number randomized.
[b]Week 12 Responder = at least 5% weight loss at Week 12; percentage calculated based on number of patients with observed Week 12 data.

TABLE 9

Week 52 Results by Week 12 Responder Status (lorcaserin 10 mg BID)

| Week 12 status | Week 52 Weight | | | |
|---|---|---|---|---|
|  | 5% Responder | 10% Responder | Mean (SE) Change from Baseline, kg | Mean (SE) Percent Change from Baseline, % |
| Pooled BLOOM and BLOSSOM Studies: (MITT with LOCF) | | | | |
| Responder (≥5% weight loss) | 85.5% | 49.8% | −10.63 (0.18) | −10.84 (0.18) |
| Non-responder (<5%) | 26.0% | 4.7% | −2.76 (0.12) | −2.73 (0.12) |
| Pooled BLOOM and BLOSSOM Studies: (Completers Population) | | | | |
| Responder (≥5% weight loss) | 85.8 | 55.9 | −11.31 (0.21) | −11.52 (0.21) |
| Non-responder (<5%) | 35.9 | 7.4 | −3.50 (0.18) | −3.44 (0.18) |
| BLOOM-DM Study: (MITT with LOCF) | | | | |
| Responder (≥5% weight loss) | 70.5 | 35.9 | −9.26 (0.77) | −9.07 (0.70) |
| Non-responder (<5%) | 25.2 | 8.6 | −3.20 (0.36) | −3.13 (0.35) |
| BLOOM-DM Study: (Completers Population) | | | | |
| Responder (≥5%) | 70.8 | 40.0 | −9.77 (0.89) | −9.49 (0.80) |
| Non-responder (<5%) | 29.0 | 10.0 | −3.45 (0.44) | −3.36 (0.42) |

[a]Week 12 Responder = at least 5% weight loss at Week 12; percentage calculated based on number of patients with observed Week 12 data.
Note:
Only patients with observed Week 12 data are included in the above analyses.

TABLE 10

Week 52 Secondary Endpoint Results by Week 12 Responder Status (lorcaserin 10 mg BID)

| Week 12 status | Week 52 Change from Baseline Mean (SE) | | | |
|---|---|---|---|---|
|  | Systolic BP | Diastolic BP | Heart Rate | HbA1c |
| Without T2DM | | | | |
| Responder (5%) | −3.39 (0.34) | −2.52 (0.25) | −2.45 (0.26) | −0.18 (0.01) |
| Nonresponder (5%) | −0.82 (0.34) | −1.02 (0.25) | −0.29 (0.26) | −0.05 (0.01) |
| With T2DM | | | | |
| Responder (5%) | −2.59 (1.73) | −1.91 (1.01) | −3.24 (1.21) | −1.20 (0.11) |
| Nonresponder (5%) | −0.55 (1.11) | −1.07 (0.86) | −0.87 (0.73) | −0.84 (0.09) |

Note:
Only patients with observed Week 12 data are included in the above analyses.

Example 4

Salts

Form III of Compound 1 hydrochloride salt hemihydrate can be prepared as described in WO 2003/086303, WO 2005/019179, WO 2006/069363, WO 2007/120517, WO 2008/070111, and WO 2009/111004, WO 2010/148207, WO/2011/153206, WO/2012/030939, WO/2012/030938, WO/2012/030951, WO/2012/030953, WO/2012/030957, and WO/2012/030927, each of which is incorporated herein by reference in its entirety.

Various synthetic routes to (R)-8-chloro-1-methyl-2,3,4,5-tetrahydro-1H-3-benzazepine, its related salts, enantiomers, crystalline forms, and intermediates, have been reported in WO 2003/086303, WO 2005/019179, WO 2006/069363, WO 2007/120517, WO 2008/070111, and WO 2009/111004, WO 2010/148207, WO/2011/153206, WO/2012/030939, WO/2012/030938, WO/2012/030951, WO/2012/030953, WO/2012/030957, and WO/2012/030927, each of which is incorporated herein by reference in its entirety.

Other uses of the disclosed methods will become apparent to those in the art based upon, inter alia, a review of this patent document.

What is claimed is:

1. A method of weight management for an individual in need thereof comprising:

treating the individual for 12 weeks with (R)-8-chloro-1-methyl-2,3,4,5-tetrahydro-1H-3-benzazepine or a pharmaceutically acceptable salt, solvate or hydrate thereof wherein the individual is administered a dose equivalent to 20 mg of (R)-8-chloro-1-methyl-2,3,4,5-tetrahydro-1 H-3-benzazepine hydrochloride per day, and continuing said treatment if the individual has achieved at least 5% weight loss by week 12, whereby achievement of at least 5% weight loss by week 12 correlates with a likelihood of the individual achieving an additional decrease in an assessment of weight after about one year, wherein the method further comprises administering a reduced-calorie diet to the individual, wherein, prior to beginning the treatment, the individual has an initial body mass index (BMI) of >27 kg/m$^2$, and wherein the pharmaceutical composition is administered orally to the individual.

2. The method of claim 1, wherein the individual has an initial BMI >30kg/m$^2$.

3. The method of claim 1, wherein the individual has at least one weight-related comorbid condition.

4. The method of claim 3, wherein the weight-related comorbid condition is selected from: hypertension, dyslipidemia, and type 2 diabetes.

5. The method of claim 1, wherein weight management comprises weight loss.

6. The method of claim 1, wherein weight management comprises controlling weight gain.

7. The method of claim 1, wherein weight management comprises maintenance of weight loss.

8. The method of claim 1, wherein the method further comprises prescribing and/or administering a program of regular exercise to the individual.

9. A method of decreasing food intake in an individual in need thereof comprising:

treating the individual for 12 weeks with (R)-8-chloro-1-methyl-2,3,4,5-tetrahydro-1H-3-benzazepine or a pharmaceutically acceptable salt, solvate or hydrate thereof, wherein the individual is administered a dose equivalent to 20 mg of (R)-8-chloro-1-methyl-2,3,4,5-tetrahydro-1 H-3-benzazepine hydrochloride per day, and continuing said treatment if the individual has achieved at least 5% weight loss by week 12, whereby achievement of at least 5% weight loss by week 12 correlates with a likelihood of the individual achieving an additional decrease in an assessment of weight after about one year, wherein the method further comprises administering a reduced-calorie diet to the individual, wherein, prior to beginning the treatment, the individual has an initial body mass index (BMI) of >27 kg/m$^2$, and wherein the pharmaceutical composition is administered orally to the individual.

10. The method of claim 9, wherein the individual has an initial BMI >30kg/m$^2$.

11. The method of claim 9, wherein the individual has at least one weight-related comorbid condition.

12. The method of claim 11, wherein the weight-related comorbid condition is selected from: hypertension, dyslipidemia, and type 2 diabetes.

13. The method of claim 9, wherein the method further comprises prescribing and/or administering a program of regular exercise to the individual.

14. A method of inducing satiety in an individual in need thereof comprising:

treating the individual for 12 weeks with (R)-8-chloro-1-methyl-2,3,4,5-tetrahydro-1H-3-benzazepine or a pharmaceutically acceptable salt, solvate or hydrate thereof, wherein the individual is administered a dose equivalent to 20 mg of (R)-8-chloro-1-methyl-2,3,4,5-tetrahydro-1 H-3-benzazepine hydrochloride per day, and continuing said treatment if the individual has achieved at least 5% weight loss by week 12,whereby achievement of at least 5% weight loss by week 12 correlates with a likelihood of the individual achieving an additional decrease in an assessment of weight after about one year, wherein the method further comprises administering a reduced-calorie diet to the individual, wherein, prior to beginning the treatment, the individual has an initial body mass index (BMI)of >27 kg/m$^2$, and wherein the pharmaceutical composition is administered orally to the individual.

15. The method of claim 14, wherein the individual has an initial BMI >30kg/m$^2$.

16. The method of claim 14, wherein the individual has at least one weight-related comorbid condition.

17. The method of claim 16, wherein the weight-related comorbid condition is selected from: hypertension, dyslipidemia, and type 2 diabetes.

18. The method of claim 14, wherein the method further comprises prescribing and/or administering a program of regular exercise to the individual.

19. A method of treating obesity in an individual in need thereof comprising:

treating the individual for 12 weeks with (R)-8-chloro-1-methyl-2,3,4,5-tetrahydro-1H-3-benzazepine or a pharmaceutically acceptable salt, solvate or hydrate thereof, wherein the individual is administered a dose equivalent to 20 mg of (R)-8-chloro-1methyl-2,3,4,5-tetrahydro-1 H-3-benzazepine hydrochloride per day, and continuing said treatment if the individual has achieved at least 5% weight loss by week 12, whereby achievement of at least 5% weight loss by week 12 correlates with a likelihood of the individual achieving an additional decrease in an assessment of weight after about one year, wherein the method further comprises administering a reduced-calorie diet to the individual, wherein, prior to beginning the treatment, the individual has an initial body mass index (BMI)of >30 kg/m$^2$, and wherein the pharmaceutical composition is administered orally to the individual.

20. The method of claim 19, wherein the individual has at least one weight-related comorbid condition.

21. The method of claim 20, wherein the weight-related comorbid condition is selected from: hypertension, dyslipidemia, and type 2 diabetes.

22. The method of claim 19, wherein the method further comprises prescribing and/or administering a program of regular exercise to the individual.

* * * * *

UNITED STATES PATENT AND TRADEMARK OFFICE
CERTIFICATE OF CORRECTION

Page 1 of 1

PATENT NO. : 9,169,213 B2
APPLICATION NO. : 14/242442
DATED : October 27, 2015
INVENTOR(S) : Matilde Sanchez and William R. Shanahan It is certified that error appears in the above-identified patent and that said Letters Patent is hereby corrected as shown below:

In the claims,

Column 41; lines 17-18, Claim 1; please replace:
"the individual has an initial body mass index (BMI) of >27 kg/m$^2$" with "the individual has an initial body mass index (BMI) of ≥27 kg/m$^2$"

Column 41; lines 21-22, Claim 2; please replace:
"wherein the individual has an initial BMI >30kg/m$^2$" with "wherein the individual has an initial BMI ≥30kg/m$^2$"

Column 41; lines 52-53, Claim 9; please replace:
"the individual has an initial body mass index (BMI) of >27 kg/m$^2$" with "the individual has an initial body mass index (BMI) of ≥27 kg/m$^2$"

Column 41; lines 56-57, Claim 10; please replace:
"wherein the individual has an initial BMI >30kg/m$^2$" with "wherein the individual has an initial BMI ≥30kg/m$^2$"

Column 42; lines 20-21, Claim 14; please replace:
"the individual has an initial body mass index (BMI) of >27 kg/m$^2$" with "the individual has an initial body mass index (BMI) of ≥27 kg/m$^2$"

Column 42; lines 24-25, Claim 15; please replace:
"wherein the individual has an initial BMI >30kg/m$^2$" with "wherein the individual has an initial BMI ≥30kg/m$^2$"

Column 42; lines 50-51, Claim 19; please replace:
"the individual has an initial body mass index (BMI) of >30 kg/m$^2$" with "the individual has an initial body mass index (BMI) of ≥30 kg/m$^2$"

Signed and Sealed this
Twenty-third Day of February, 2016

Michelle K. Lee
*Director of the United States Patent and Trademark Office*